(12) United States Patent
Shepard

(10) Patent No.: US 7,138,388 B2
(45) Date of Patent: Nov. 21, 2006

(54) METHODS TO TREAT AUTOIMMUNE AND INFLAMMATORY CONDITIONS

(75) Inventor: H. Michael Shepard, Encinitas, CA (US)

(73) Assignee: Celmed Oncology (USA), Inc., Quebec (CA)

( * ) Notice: Subject to any disclaimer, the term of this patent is extended or adjusted under 35 U.S.C. 154(b) by 0 days.

(21) Appl. No.: 10/051,320

(22) Filed: Jan. 18, 2002

(65) Prior Publication Data

US 2002/0151519 A1 Oct. 17, 2002

Related U.S. Application Data

(60) Provisional application No. 60/262,849, filed on Jan. 19, 2001.

(51) Int. Cl.
*A61K 31/685* (2006.01)
*A61K 31/70* (2006.01)
*A61K 31/66* (2006.01)

(52) U.S. Cl. ............................ 514/80; 514/50; 514/51; 514/108; 514/107; 514/118

(58) Field of Classification Search ................ 514/80, 514/50, 51, 108, 107, 118
See application file for complete search history.

(56) References Cited

U.S. PATENT DOCUMENTS

| | | | |
|---|---|---|---|
| 3,852,266 A | 12/1974 | Kiyanagi et al. |
| 4,247,544 A | 1/1981 | Bergstrom et al. |
| 4,267,171 A | 5/1981 | Bergstrom et al. |
| 4,542,210 A | 9/1985 | Sakata et al. |
| 4,816,570 A | 3/1989 | Farquhar |
| 4,948,882 A | 8/1990 | Ruth |
| 4,975,278 A | 12/1990 | Senter et al. |
| 5,070,082 A | 12/1991 | Murdock et al. |
| 5,077,282 A | 12/1991 | Murdock et al. |
| 5,077,283 A | 12/1991 | Murdock et al. |
| 5,085,983 A | 2/1992 | Scanlon |
| 5,116,827 A | 5/1992 | Murdock et al. |
| 5,212,161 A | 5/1993 | Moriniere et al. |
| 5,212,291 A | 5/1993 | Murdock et al. |
| 5,233,031 A | 8/1993 | Borch et al. |
| 5,264,618 A | 11/1993 | Felgner et al. |
| 5,457,187 A | 10/1995 | Gmeiner et al. |
| 5,459,127 A | 10/1995 | Felgner et al. |
| 5,521,161 A | 5/1996 | Malley et al. |
| 5,616,564 A | 4/1997 | Rapaport |
| 5,627,165 A | 5/1997 | Glazier |
| 5,643,893 A | 7/1997 | Benson et al. |
| 5,645,988 A | 7/1997 | Vande Woude et al. |
| 5,663,321 A | 9/1997 | Gmeiner et al. |
| 5,705,336 A | 1/1998 | Reed et al. |
| 5,798,340 A | 8/1998 | Bischofberger et al. |
| 5,981,507 A | 11/1999 | Josephson et al. |
| 6,245,750 B1 | 6/2001 | Shepard |
| 6,589,941 B1 | 7/2003 | Fahrig et al. |
| 6,599,499 B1 * | 7/2003 | Rosen et al. ................ 424/9.34 |

FOREIGN PATENT DOCUMENTS

| | | |
|---|---|---|
| GB | 982776 | 2/1965 |
| WO | WO 91/17424 | 11/1991 |
| WO | WO 93/06120 A1 | 4/1993 |
| WO | WO 94/03467 | 2/1994 |
| WO | WO 94/22483 | 10/1994 |
| WO | WO 95/08556 | 3/1995 |
| WO | WO 96/03151 A2 | 2/1996 |
| WO | WO 96/07413 A1 | 3/1996 |
| WO | WO 96/10030 | 4/1996 |
| WO | WO 96/29336 | 9/1996 |
| WO | WO 96/40088 | 12/1996 |
| WO | WO 96/40708 | 12/1996 |
| WO | WO 97/28179 | 8/1997 |
| WO | WO 99/08110 | 2/1999 |
| WO | WO 99/20741 | 4/1999 |
| WO | WO 99/23104 | 5/1999 |
| WO | WO 99/37753 | 7/1999 |
| WO | WO 01/07088 A2 | 2/2001 |
| WO | WO 01/07454 A1 | 2/2001 |
| WO | WO 01/36686 A2 | 5/2001 |
| WO | WO 2004/011625 A2 | 2/2004 |

OTHER PUBLICATIONS

Lackey et al. Enzyme-catalyzed therapeutic agent (ECTA) design: activation of the antitumor ECTA compound NB1011 by thymidylate synthase. Biochemical Pharmacology 2001, 61(2) pp. 179-189.*

Abraham, T.W., et al. (1996) "Synthesis and biological activity of aromatic amino acid phosphoramidates of 5-fluoro-2'-deoxyuridine and 1-β-arabinofuranosylcytosine: Evidence of phosphoramidase activity" *J. Med. Chem.* 39:4569-4575.

(Continued)

*Primary Examiner*—Shengjun Wang
*Assistant Examiner*—Jennifer Kim
(74) *Attorney, Agent, or Firm*—Foley & Lardner LLP

(57) ABSTRACT

This invention provides methods for treating inflammatory or autoimmune diseases by contacting the affected cell or tissue with a therapeutic compound as described herein. Such pathologies include, but are not limited to rheumatoid arthritis, systemic lupus erythmatosus, psoriatic arthritis, reactive arthritis, Crohn's disease, ulcerative colitis and scleroderma. Therapeutic compounds useful in the methods of this invention are selected from the group consisting of a 1,5-substituted pyrimidine derivative or analog and substituted furano-pyrimidone analog.

2 Claims, 3 Drawing Sheets

OTHER PUBLICATIONS

Akdas, A., et al. (1996) "Glutathione S-transferase and multidrug-resistant phenotype in transitional cell carcinoma of the bladder" *Eur. Urol.* 29:483-486.

Almasan, A., et al. (1995) "Genetic instability as a consequence of inappropriate entry into and progression through S-phase" *Cancer & Metastasis Rev.* 14:59-73.

Almasan, A., et al. (Jun. 1995) "Deficiency of retinoblastoma protein leads to inappropriate S-phase entry, activation of E2F-responsive genes, and apoptosis" *PNAS*, USA 92:5436-5440.

Andersen, T.I., et al. (1995) "Detection of c-erbb-2 related protein in sera from breast cancer patients" *Acta Oncol.* 34(4):499-504.

Anglada, J.M., et al. (Jul.-Aug. 1996) "$N,N'$-cyclization of carbodiimides with 2-(bromomethyl)acrylic acid. A direct entry to the system 5-methylene-$6H$-pyrimidine-2,4-dione, a new class of thymine analogues" *J. Heterocyclic Chem.* 33:1259-1270.

Antelman, D., et al. (1995) "Inhibition of tumor cell proliferation *in vitro* and *in vivo* by exogenous $p110^{RB}$, the retinoblastoma tumor suppressor protein" *Oncogene* 10:697-704.

Asakura, J., et al. (1988) "Cerium(IV) catalyzed iodination at C5 of uracil nucleosides" *Tetrahedron Lett.* 29(23):2855-2858.

Asakura, J., et al. (1990) "Cerium(IV)-mediated halogenation at C-5 of uracil derivatives" *J. Org. Chem.* 55:4929-4933.

Aschele, C. et al. (Jun. 1999) "Immunohistochemical quantitation of thymidylate synthase expression in colorectal cancer metastases predicts for clinical outcome to fluorouracil-based chemotherapy" *J. Clin. Oncol.* 17(6):1760-1770.

Ayisi, N. K., et al. (1933) "Comparison of the antiviral effects of 5-methoxymethyldeoxyuridine-5'-monophosphate with adenine arabinoside-5'-monophosphate" *Antiviral Res.* 3:161-174.

Balzarini, J., et al. (1987) "Thmidylate synthase is the principal target enzyme for the cytostatic activity of ($E$)-5-(2-bromovinyl)-2'-deoxyuridine against murine mammary carcinoma (FM3A) cells transformed with the herpes simplex virus type 1 or type 2 thymidine kinase gene" *Mol. Pharmacol.* 32:410-416.

Balzarini, J., et al. (1993) "Differential mechanism of cytostatic effect of ($E$)-5-(2-bromovinyl)-2'-deoxyuridine, 9-(1,3-dihydroxy-2-propoxymethyl)guanine, and other antiherpetic drugs on tumor cells transfected by the thymidine kinase gene of herpes simplex virus type 1 or type 2" *J. Biol. Chem.* 268(9):6332-6337.

Balzarini, J., et al. (1995) "Incorporation of 5-substituted pyrimidine nucleoside anologues into DNA of a thymidylate synthetase-deficient murine FM3A carcinoma cell line" *Meth. Find. Exptl. Clin. Pharmacol.* 7(1):19-28.

Balzarini, J., et al. (1996) "Anti-HIV and anti-HIV activity and resistance profile of 2',3'-dideoxy-3'-thiacytidine (3TC) and its arylphosphoramidate derivative CF 1109" *Biochem. Biophys. Res. Commun.* 225:363-369.

Balzarini, J., et al. (1997) "Conversion of 2',3'-dideoxyadenosine (ddA) and 2',3'-didehydro-2',3'-dideoxyadenosine (d4A) to their corresponding aryloxyphosphoramidate derivatives markedly potentiates their activity against human immunodeficiency virus and hepatitis B virus" *FEBS Lett.* 410:324-328.

Balzarini, J., et al. (Jul. 1996) "Mechanism of anti-HIV action of masked alaninyl d4T-MP derivatives" *PNAS USA* 93:7295-7299.

Banerjee, D., et al. (1995) "Molecular mechanisms of resistance to antifolates, a review" *Acta Biochemical Polonica* 42(4):457-464.

Banerjee, D., et al. (Oct. 1998) "Role of E2F-1 in chemosensitivity" *Can. Res.* 58:4292-4296.

Barbato, S., et al. (1989) "Synthesis of bridged pyrimidine nucleosides and triazo [4, 3-c] pyrimidine nucleoside analogues" *Nucleosides & Nucleotides* 8(4):515-528.

Barbour, K.W., et al. (1992) "A naturally occurring tyrosine to histidine replacement at residue 33 of human thymidylate synthase confers resistance to 5-fluoro-2'-deoxyuridine in mammalian and bacterial cells" *Mol. Pharmacol.* 42:242-248.

Barr, P.J., et al. (1981) "Inhibition of thymidylate synthetase by 5-alkynyl-2'-deoxyuridylates" *J. Med. Chem.* 24(12):1385-1388.

Barr, P.J., et al. (1983) "Reaction of 5-ethynyl-2'-deoxyuridylate with thiols and thymidylate synthetase" *Biochem.* 22:1696-1703.

Barr, P.J., et al. (1983) "Thymidylate synthetase-catalyzed conversions of $E$-5-(2-Bromovinyl)-2'-deoxyuridylate" *J. Biol. Chem.* 258(22):13627-13631.

Barrett, J.E., et al. (1998) "Trapping of the C5 methylene intermediate in thymidylate synthase" *J. Am. Chem. Soc.* 120:449-450.

Belt, J.A., et al. (1993) "Nucleoside Transport in Normal and Neoplastic Cells" *Advan. Enzyme Regul.* 33:235-252.

Benzaria, S., et al. (1996) "Synthesis, *in vitro* antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability" *J. Med. Chem.* 39:4958-4965.

Bergstrom, D.E., et al. (1981) "C-5 substituted pyrimidine nucleosides. 3. Reaction of allylic chlorides, alcohol, and acetates with pyrimidine nucleoside derived organopalladium intermediates" *J. Org. Chem.* 46(7):1432-1441.

Bergstrom, D.E., et al.(1984) "Synthesis of ($E$)-5-(3,3,3-trifluoro-1-propenyl)-2'-deoxyuridine and related analogues: potent and unusually selective antiviral activity of ($E$)-5-(3,3,3-trifluoro-1-propenyl)-2'-deoxyuridine against herpes simplex virus type 1" *J. Med. Chem.* 27:279-284.

Bertino, J.R., et al. (1996) "Resistance mechanism to methotrexate in tumors" *Stem Cells* 14:5-9.

Berkow, R., et al. (1992) "The Merck Manual of Diagnosis and Therapy" 16th Edition, Merck & Co., Rahway, New Jersey, p. 1278.

Bible, K.C. et al. (Aug. 15, 1997) "Cytotoxic Surgery between Flavopiridol (NSC 649890, L86-8275) and Various Antineoplastic Agents: The Importance of Sequence of Administration" *Cancer Res.* 57:3375-3380.

Bigge, C.F., et al. (1980) "Palladium-catalyzed coupling reactions of uracil nucleosides and nucleosides" *J. Am. Chem. Soc.* 102(6):2033-2038.

Bosslet, K., et al. (1995) "A novel one-step tumor-selective prodrug activation system" *Tumor Targetting* 1:45-50.

Bosslet, K., et al. (Mar. 15, 1998) "Elucidation of the mechanism enabling tumor selective prodrug monotherapy" *Cancer Res.* 58:1195-1201.

Brison, O. (1993) "Gene amplification and tumor progression" *Biochem. Biophys. Acta* 1155:25-41.

Budavari, S. (Jul. 1996) (Ed.), "The Merck Index" 12th Edition Doxifluridine, p. 3493.

Budavari, S. (Jul. 1996) (Ed.), "The Merck Index" 12th Edition Floxuridine, p. 4148.

Budavari, S. (Jul. 1996) (Ed.), "The Merck Index" 12th Edition Idoxuridine, p. 4934.

Carl, P.L., et al. (1980) "Protease-activated 'prodrugs' for cancer chemotherapy" *PNAS USA* 77(4):2224-2228.

Carreras, C.W., et al. (1995) "The catalytic mechanism and structure of thymidylate synthase" *Annu. Rev. Biochem.* 64:721-762.

Carter, P., et al. (May 1992) "Humanization of an anti-p185[HER2] antibody for human cancer therapy" *PNAS USA* 89:4285-4289.

Cava, M.P., et al. (1985) "Thionation reactions of lawesson's reagents" *Tetrahedron* 41(22):5061-5087.

Chakravarty, P.K., et al. (1983) "Plasmin-activated prodrugs for cancer chemotherapy. 2. Synthesis and biological activity of peptidyl derivatives of doxorubicin" *J. Med. Chem.* 26(5):638-644.

Chaudhuri, N.C., et al. (1995) "Very high affinity DNA recognition by bicyclic and cross-linked oligonucleotides" *J. Am. Chem. Soc.* 117:10434-10442.

Chen, L., et al. (Mar. 15, 1996) "Sensitization of human breast cancer cells to cyclophosphamide and ifosfamide by transfer of a liver cyctochrome P450 gene" *Can. Res.* 56:1331-1340.

Cho, Y.M., et al. (1994) "($E$)-5-(3-oxopropen-1-yl)-2'-deoxyuridine and ($E$)-5-(3-oxopropen-1-yl)-2',3'-dideoxyuridine; new antiviral agents: Syntheses and biological activity" *Tetrahedron Lett.* 35(8):1149-1152.

Chou, T.C., et al. (1984) "Quantitative Analysis of Dose-Effect Relationships: The Combined Effects of Multiple Drugs or Enzyme Inhibitors" *Adv. Enzyme Regul.* 22:27-55.

Clarke, R., et al. (1996) "Animal models of breast cancer. Their diversity and role in biomedical research" *Breast Can. Res. & Treatment* 39:1-6.

Colacino, J.M. (1996) "Mechanisms for the anti-hepatitis B virus activity and mitochondrial toxicity of fialuridine (FIAU)" *Antiviral Res.* 29:125-139.

Collins, J.M., et al. (Aug. 1999) "Suicide Prodrugs Activated by Thymidylate Synthase: Rationale for Treatment and Noninvasive Imaging of Tumors with Deoxyuridine Analogues" *Clin. Cancer Res.* 5:1976-1981.

Connors, T.A. (1986) "Prodrugs in cancer chemotherapy" *Xenobiotica* 16(10/11):975-988.

Connors, T.A. (1996) "Is there a future for cancer chemotherapy" *Annals Oncol.* 7:445-452.

Connors, T.A., et al. (1995) "Prodrugs in cancer chemotherapy" *Stem Cells* 13:501-511.

Copur, S., et al. (1995) "Thymidylate synthase gene amplification in human colon cancer cell lines resistant to 5-flouorouracil" *Biochem. Pharmacol.* 49(10):1419-1426.

Crisp, G.T. (1989) "Synthesis of 5-alkenyl-2'-deoxyuridines via organostannanes" *Synthetic Commun.* 19(11&12):2117-2123.

Cruickshank, K.A., et al. (1988) "Oligonucleotide labeling: A concise synthesis of a modified thymidine phoporamidite" *Tetrahedron Lett.* 29(41):5221-5224.

Curtin, N.J., et al. (May 1, 1991) "Mechanism of Cell Death following Thymidylate Synthase Inhibition: 2'-Deoxyuridine-5'-triphosphate Accumulation, DNA Damage, and Growth Inhibition following Exposure to CB3717 and Dipyridamole" *Cancer Res.* 51:2346-2352.

Dagle, J.M., et al. (Aug. 25, 1990) "Targeted Degradation of mRNA in *Xenopus oocytes* and Embryos Directed by Modified Oligonucleotides: Studies of An2 and Cyclin in Embryogenesis" *Nucleic Acids Research* 18(16):4751-4757.

Dale, R.M.K., et al. (Aug. 1973) "The synthesis and enzymatic polymerization of nucleotides containing mercury: Potential tools for nucleic acid sequencing and structural analysis" *PNAS USA* 70(8):2238-2242.

Davisson, V.J., et al. (1989) "Expression of human thymidylate synthase in *Escherichia coli*" *J. Biol. Chem.* 264(16):9145-9148.

Davisson, V.J., et al. (1994) "Expression of human thymidylate synthase in *Escherichia coli*. (Additions and corrections)" *J. Biol. Chem.* 269(48):30740.

De Clercq, E. (1994) "Antiviral Activity Spectrum and Target of Action of Different Classes of Nucleoside Analogues" *Nucleosides & Nucleosides* 13(6&7):1271-1295.

De Clercq, E., et al. (1983) "Nucleic acid related compounds. 40. Synthesis and biological activities of 5-alkynyluracil nucleosides" *J. Med. Chem.* 26:661-666.

De Clercq, E., et al. (Sep. 18, 1978) "Antiviral Activity of Novel Deoxyuridine Derivatives" *Current Chemotherapy: Proceedings of the International Congress of Chemotherapy* 1:352-354.

De Clercq, E., et al. (Oct. 1997) "In Search of a Selective Antiviral Chemotherapy" *Clin. Microbiol. Rev.* 10(4):674-693.

Dicker, A.P., et al. (Dec. 1993) "Methotrexate resistance in an *in vivo* mouse tumor due to a non-active-site dihydrofolate reductase mutation" *PNAS USA* 90:11797-11801.

Dirven, H.A.A.M., et al. (Apr. 15, 1995) "The role of human glutathione S-transferase isoenzymes in the formation of glutathione conjugates of the alkylating cytostatic drug thiotepa" *Can. Res.* 55:1701-1706.

Dorr, R.T., et al. (1994) "PALA" In: Cancer Chemotherapy Handbook: Appleton & Lange, Norwalk, Connecticut: 768-773.

Drake, J.C., et al. (1996) "Resistance to Tomudex (ZD1694): Multifactorial in Human Breast and Colon Carcinoma Cell Lines" *Biochem. Pharacol.* 51:1349-1355.

Dunn III, W.J., et al. (1996) "Solution of the comformation and alignment tensors for the binding of trimethoprim and its analogs to dihydrofolate reductase: 3D-quantitative structure-activity relationship study using colecular shape analysis, 3-way partial least-squares regression, and 3-way factor analysis" *J. Med. Chem.* 39:4825-4832.

Dyer, R.L., et al., "The synthesis of E-5-(2-bromovinyl)-2'-deoxyuridine from 2'-deoxy-5-iodouridine" in: Nucleic Acid Chemistry: Improved and New Synthetic Procedures, Methods and Techniques, Townsend et al. (Eds.), John Wiley & Sons, Inc., New York, pp. 79-83, 2000.

Eccles, S.A., et al. (1994-1995) "Signigicance of the c-erbβ family of receptor tyrosine kinases in metastatic cancer and their potential as targets for immunotherapy" *Invasion Metastasis* 14:337-348.

Edler, D., et al. (Feb. 2000) "Immunohistochemically detected thymidylate synthase in colorectal cancer: An independent prognostic factor of survival" *Clinical Cancer Research* 6:488-492.

Eisenbrand, G., et al. (1996) "An approach towards more selective anticancer agents" *J. Synthetic Organic Chem.* 10:1246-1258.

Evrard, A., et al. (1996) "An in vitro nucleoside analog screening method for cancer gene therapy" *Chem. Abstracts* 126:Abstract No. 26514, Issue No. 3, p. 32, Jan. 20, 1997.

Evrard, A., et al. (1996) "An in vitro nucleside analog screening method for cancer gene therapy" *Cell Biol. Toxicol.* 12:345-350.

Fan, J., et al. (1997) "Functional roles of E2F in cell cycle regulation" *Oncogene* 14:1191-1200.

Farquhar, D., et al. (1994) "Synthesis and antitumor evaluation of bis(pivaloyloxy)methyl 2'-deoxy-5-fluorouridine 5'-monophosphate (FdUMP): A strategy to introduce nucleotides into cells" *J. Med. Chem.* 37:3902-3909.

Farquhar, D., et al. (1995) "5'-[4-(pivaloyloxy)-1,3,2-dioxaphosphorinan-2-yl]-2'-deoxy-5-fluorouridine: A membrane-permeating prodrug of 5-fluoro-2'-deoxyuridylic acid (FdUMP)" *J. Med. Chem.* 38:488-495.

Felip, E., et al. (1995) "Overexpression of c-*erb*β-2 in epithelia ovarian cancer" *Cancer* 75(8):2147-2152.

Finch, S.C., et al. (1991) "Radiation Injury" In: Harrison's Principles of Internal Medicine, $12^{th}$ edition: McGraw-Hill, Inc., New York, NY:2004-2208.

Finer-Moore, J., et al. (1993) "Refined structures of substrate-bound and phosphate-bound thymidylate synthase from *Lactobacillus casei*" *J. Mol. Biol.* 232:1101-1116.

Finer-Moore, J.S., et al. (1994) "Crystal structure of thymidylate synthase from T4 phage: Component of a deoxynucleoside triphophate-synthesizing complex" *Biochem.* 33:15459-15468.

Firestone, W.M., et al. (May 1990) "A comparison of the effects of antitumor agents upon normal human epidermal kerarinocytes and human squamous cell carcinoma" *J. Investigative Dermatol.* 94:657-661.

Firestone, W.M., et al. (Jul. 2, 1990) "A comparison of the effects of antitumor agents upon normal human epidermal keratinocytes and human squamous cell carcinoma" *Chem. Abstracts* 113:Abstract No. 254.

Freed, J.J., et al. (1989) "Evidence for acyloxymethyl esters of pyrimidine 5'-deoxyribonucleotides as extracellular sources of active 5'-deoxyribonucleotides in cultured cells" *Biochem. Pharmacol.* 38(19):3193-3198.

Freemantle, S.J., et al. (1995) "Molecular characterisation of two cell lines selected for resistance to the folate-based thymidylate synthase inhibitor, ZD1694" *British Journal of Cancer* 71:925-930.

Fries, K.M., et al., (1995) "Synthesis and biological evaluation of 5-fluoro-2'-deoxyuridine phosphoramidate analogs" *J. Med. Chem.* 38(14):2672-2680.

Funk, J.O. (1999) "Cancer cell cycle control" *Anticancer Research* 19:4772-4780.

Garrett, C.G., et al. (1979) "Thymidylate synthetase. Catalysis of dehalogenation of 5-bromo-and 5-iodo-2'-deoxyuridylate" *Biochem.* 18(13):2798-2804.

Goel, R., et al. (Feb. 1989) "Selective Intraperitoneal Biochemical Modulation of Methotrexate by Dipyridamole" *J. Clin. Oncol.* 7(2):262-269.

Goldberg, J.L., et al. (1997) "Novel cell imaging techniques show induction of apoptosis and proliferation in mesothelial cells by asbestos" *Am. J. Respir. Cell Mol. Biol.* 17:265-271.

Goldstein, J.L., et al. (1991) "Genetic aspects of disease" In: Harrison's Principles of Internal Medicine, $12^{th}$ edition: McGraw-Hill, Inc., New York, NY:21-76.

Goodwin, J.T., et al. (1993) "Incorporation of alkylthiol chains at C-5 of deoxyuridine" *Tetrahedron Lett.* 34(35):5549-5552.

Gorlick, R., et al. (Dec. 1999) "Drug Resistance in Colon Cancer" *Semin. Olcol.* 26(6):606-611.

Gottesman, M.M., et al., (1995) "Genetic analysis of the multidrug transporter" *Annu. Rev. Genet.* 29:607-649.

Graham, D., et al. (1998) "DNA duplexes stabilized by modified monomer residues: synthesis and stability" *J. Chem. Soc. Perkin Trans.* 1:1131-1138.

Grem, J. L., et al. (Apr. 1992) "Biochemical Modulation of Fluorouracil by Dipyridamole: Preclinical and Clinical Experience" *Semin Oncol.* 19(2)(3):56-65.

Griffith, D. A., et al. (1990) "Differential Inhibition of Nucleoside Transport Systems in Mammalian Cells by a New Series of Compounds Related to Lidoflazine and Mioflazine" *Biochem. Pharmacol.* 40(10):2297-2303.

Gros, P., et al. (1986) "Isolation and characterization of DNA sequences amplified in multidrug-resistant hamster cells" *PNAS USA* 83:337-341.

Gros, P., et al. (1986) "Isolation and expression of a complementary DNA that confers multidrug resistance" *Nature* 323:728-7731.

Gros, P., et al. (1986) "Mammalian multidrug resistance gene: Complete cDNA sequence indicates strong homology to bacterial transport proteins" *Cell* 47:371-380.

Gudkov, A.V., et al. (1987) "Cloning and characterization of DNA sequences amplified in multidrug-resistant djungarian hamster and mouse cells" *Somat. Cell. Mol. Genet.* 13(6):609-619.

Hakimelahi, G.H., et al. (Nov. 10, 1995) Design, Synthesis and Structure-Activity Relationship of Novel Dinucleotide Analogs 38(23):4648-4659.

Hardy, L.W., et al. (1987) "Atomic structure of thymidylate synthase: Target for rational drug design" *Science* 235:448-455.

Harris, M.P., et al. (1996) "Adenovirus-mediated p53 gene transfer inhibits growth of human tumor cells expressing mutant p53 protein" *Cancer Gene Ther.* 3(2):121-130.

Hashimoto, Y., et al. (1987) "Simple separation of tritiated water and [$^3$H] deoxyuridine from [5-$^3$H] deoxyuridine 5'-monophosphate in the thymidylate synthase assay" *Anal. Biochem.* 167:340-346.

Hengstschläger, M., et al. (1996) "The role of p16 in the E2F-dependent thymidine kinase regulation" *Oncogene* 12:1635-1643.

Hobbs, F.W. (1989) "Palladium-catalyzed synthesis of alkynylamino nucleosides. A universal linker for nucleic acids" *J. Org. Chem.* 54:3420-3422.

Holý, A., et al. (1999) "Structure-Antiviral Activity Relationship in the Series of Pyrimidine and Purine N-[2-(2-Phosphonomethoxy)ethyl] Nucleotide Analogues. 1. Derivatives Substituted at the Carbon Atoms of the Base" *J. Med. Chem.* 42:2064-2086.

Horikoshi, T., et al. (1992) "Quantitation of thymidylate synthase, dihydrofloate reductase, and DT-diaphorase gene expression in human tumors using the polymerase chain reaction" *Can. Res.* 52:108-116.

Horn, D.M., et al. (1997) "Fialuridine is phosphorylated and inhibits DNA synthesis insolated rat hepatic mitochondria" *Antiviral Res.* 34:71-74.

Hostetler, K.Y., et al. (1997) "Enhanced oral absorption and antiviral activity of 1-o-octadecyl-sn-glycero-3-phospho-acyclovir and related compounds in hepatitis B virus infection, *in vitro*" *Biochem. Pharmacol.* 53:1815-1822.

Houze, T.A., et al., (1997) "Detection of thymidylate synthase gene expression levels in formalin-fixed paraffin embedded tissue by semiquantitative, nonradioactive reverse transcriptase polymerase chain reaction" *Tumor Biol.* 18:53-68.

Howell, S. B., et al. (Jun. 15, 1989) "Comparison of the Synergistic Potentiation of Etoposide, Doxorubicin, and Vinblastine Cytotoxicity by Dipyridamole" *Cancer Res.* 49:3178-3183.

Hsiao, L.Y., et al. (1981) "Synthesis of 5'-thymidinyl bis(1-aziridinyl) phosphinates as antineoplastic agents" *J. Med. Chem.* 24:887-889.

Huang, W., et al. (1997) "Active site general catalysts are not necessary for some proton transfer reactions of thymidylate synthase" *Biochem.* 36:1869-1873.

Hudziak, R.M., et al. (1990) "Selection for transformation and *met* protooncogene amplification in NIH 3T3 fibroblasts using tumor necrosis factor α" *Cell Growth & Differentiation* 1:129-134.

Hudziak, R.M., et al. (Jul. 1988) "Amplified expression of the HER2/ERBB2 oncogene induces resistance to tumor necrosis factor α in NIH 3T3 cells" *PNAS USA* 85:5102-5106.

Husain, I., et al. (Jan. 15, 1994) "Elevation of topoisomerase I messenger RNA, protein, and catalytic activity in human tumors: Demonstration of tumor-type specificity and implications for cancer chemotherapy" *Cancer Research* 54:539-546.

Husak, R., et al. (1998) "Pseudotumour of the tongue caused by herpes simplex virus type 2 in an HIV-1 infected immunosuppressed patient" *British J. Dermatol.* 139:118-121.

Imai, K., et al. (1969) "Studies on phosphorylation. IV. Selective phosphorylation of the primary hydroxyl group in nucleosides" *J. Org. Chem.* 34(6):1547-1550.

Jackman, A.L., et al. (1995) "Folate-based thymidylate synthase inhibitors as anticancer drugs" *Annals of Oncology* 6:871-881.

Jackman, A.L., et al. (1995) "Quinazoline-based thymidylate synthase inhibitors: relationship between structural modifications and polyglutamation" *Anti-Cancer Drug Design* 10:573-589.

Johnston, P.G. (1994) "The role of thymidylate synthase expression in prognosis and outcome of adjuvant chemotherapy in patients with rectal cancer" *J. Clin. Oncol.* 12(12):2640-2647.

Johnston, P.G., et al. (1991) "Production and characterization of monoclonal antibodies that localize human thymidylate synthase in the cytoplasm of human cells and tissue" *Can. Res.* 51:6668-6676.

Jones, R.G., et al. (Aug. 20, 1953) "New methods of synthesis of β-aminoethylpyrazoles" *J. Am. Cancer Res.* 75:4048-4052.

Kamb, A., et al. (1998) "Cyclin-dependent kinase inhibitors and human cancer" *Curr. Top. Microbiol. Immunol.* 227:139-148.

Kashani-Sabet, M., et al. (Oct. 15, 1988) "Detection of drug resistance in human tumors by *in vitro* enzyme amplification" *Can. Res.* 48:5775-5778.

Katki, A.G., et al. (Mar. 1998) "Prodrugs Activated by Thymidylate Synthase: Treatment of Tumors with Deoxyuridine Analogs" *Proc. Amer. Assoc. Cancer Res.* 39, Abstract No. 1275.

Klecker, R.W., et al. (1994) "Toxicity, metabolism, DNA incorporation with lack of repair, and lactate production for 1-(2'-fluoro-2'deoxy-β-D-arabinofuranosyl)-5-iodouracil in U-937 and MOLT-4 cells" *Mol. Pharmacol.* 46:1204-1209.

Knighton, D.R., et al. (1994) "Structure and kinetic channeling in bifunctional dihydrofolate reductase-thymidylate snythase" *Nature Struct. Biol.* 1(3):186-194.

Kobayashi, H., et al. (Nov. 1995) "Effect of hammerhead ribozyme against human thymidylate synthase on the cytotoxicity of thymidylate synthase inhibitors" *Jpn. J. Can. Res.* 86:1014-1018.

Kodama, E., et al. (1996) "Evaluation of antiherpetic compounds using a gastric cancer cell line: Prounounced activity of BVDU against herpes simples virus replication" *Microbiol. Immunnol.* 40(5):359-363.

Krajewska, E., et al. (1982) "Pyrimidine ribonucleoside phosphorylase activity VS 5- and/or 6-substituted uracil and uridine analogues, including conformational aspects" *Biochem. Pharmacol.* 31(6):1097-1102.

Kraupp, M., et al. (1995) "Membrane Transport of Nucleobases: Interaction with Inhibitors" *Gen. Pharmacol.* 26(6):1185-1190.

Kumar, A., et al. (1990) "Synthesis and Biological Evaluation of Some Cyclic Phosphoramidate Nucleoside Derivatives" *J. Med. Chem.* 33(9):2368-2735.

Kundu, N.G. (1993) "Synthesis and biological activities of [E]-5-(2-acylvinyl) uracils" *Eur. J. Med. Chem.* 28:473-479.

Kuroboshi, M., et al. (1991) "A facile synthesis of difluoromethylene compounds by oxidative fluorodesulfurization of dithioacetals using tetrabutylammonium dihydrogentrifluoride and N-halo compounds" *SYNLETT*:909-910.

Kuroboshi, M., et al. (1994) "A facile synthesis of α,α-difluoroalkyl ethers and carbonyl fluoride acetals by oxidative desulfurization-fluorination" *SYNLETT*:251-252.

Lackey, D. B., et al. (2001) "Enzyme-catalyzed therapeutic agent (ECTA) design: activation of the antitumor ECTA compound NB1011 by thymidylate synthase" *Biochem. Pharmacol.* 61:179-189.

Lam, K.S. (1997) "Application of combinatorial library methods in cancer research and drug discovery" *Anticancer Drug Design* 12:145-167.

Larsson, P.A., et al. (1996) "Thymidylate Synthase in Advanced Gastrointestinal and Breast Cancers" *Acta Oncological* 35(4):469-472.

Lasic, D.D. (Apr. 11, 1996) "Doxorubicin in sterically stabilized liposomes" *Nature* 380:561-562.

Lee, Y.L., et al. (1997) "Inhibition of mouse thymidylate synthase promoter activity by the wild-type p53 tumor suppressor protein" *Exp. Cell Res.* 234:270-276.

Lehman, N. L., et al. (2000) "Modulation of RTX cytotoxicity by thymidine and dipyridamole in vitro: implications for chemotherapy" *Cancer Chemother. Pharmacol.* 45:142-148.

Leichman, C. G., et al. (Oct. 1997) "Quantitation of Intratumoral Thymidylate Synthase Expression Predicts for Disseminated Colorectal Cancer Response and Resistance to Protracted-Infusion Fluorouracil and Weekly Leucovorin" *J. Clin. Oncol.* 15(10):3223-3229.

Lenz, H.J., et al. (May 1998) "p53 and thymidylate synthase expression in untreated stage II colon cancer: Associations with recurrence, survival, and site" *Clinical Cancer Research* 4:1227-1234.

Les, A., et al. (1998) "Modeling of reaction steps relevant to deoxyuridylate (dUMP) enzymatic methylation and thymidylate synthase mechanism-based inhibition" *Journal of Biomolecular Structure & Dynamics* 15(4):703-715.

Lewis, J.G., et al. (Apr. 1996) "A serum-resistant cytofectin for cellular delivery of antisense oligodeoxynucleotides and plasmid DNA" *PNAS USA* 93:3176-3181.

Li, W., et al. (1995) "Lack of functional retinoblastoma protein mediates increased resistance to antimetabolites in human sarcoma cell lines" *PNAS USA* 92:10436-10440.

Lin, W.Y., et al. (1997) "Rhenium-188 hydroxyethylidene diphosphonate: A new generator-produced radiotherapeutic drug of potential value for the treatment of bone metastases" *Eur. J. Nucl. Med.* 24(6):590-595.

Livak, K.J., et al. (1992) "Detection of single base differences using biotinylated nucleotides with very long linker arms" *Nucl. Acids Res.* 20(18):4831-4837.

Livingstone, L.R., et al. (1992) "Altered cell cycle arrest and gene amplification potential accompany loss of wild-type p53" *Cell* 70:923-935.

Lönn, U., et al. (1996) "Higher frequency of gene amplification in breast cancer patients who received adjuvant chemotherapy" *Cancer* 77(1):107-112.

Look, K.Y., et al. (1997) "Increased thymidine kinase and thymidylate synthase activities in human epithelial ovarian carcinoma" *Anticancer Res.* 17:2353-2356.

Lovejoy, E.A., et al. (1997) "Animal models and the molecular pathology of cancer" *J. Pathol.* 181:130-135.

Madec, A., et al. (1998) "Some characteristics of fetal and adult isoenzymes of thymidine kinase in human breast cancers" *Bull. Cancer* 75:187-194.

Mader, R.M., et al. (1998) "Resistance to 5-fluorouracil" *Gen. Pharma.* 31(5):661-666.

Mahony, C., et al. (Mar. 1982) "Dipyridamole Kinetics" *Clin. Pharmacol. Ther.* 31(3):330-338.

Masters, J.N., et al. (1983) "The nucleotide sequence of the c DNA coding for the human dihydrofolic acid reductase" *Gene* 21:59-63.

McGuigan, C. (1992) "Aryl phosphate derivative of AZT retain activity HIV1 in cell lines which are resistant to the action of AZT" *Antiviral Res.* 17:311-321.

McGuigan, C. (1993) "Intracellular delivery of bioactive AZT nucleotides by aryl phosphate derivatives of AZT" *J. Med. Chem.* 36:1048-1052.

McGuigan, C. (1996) "Aryl phosphoramidate derivatives of d4T have improved anti-HIV efficacy in tissue culture and may act by the generation of a novel intracellular metabolite" *J. Med. Chem.* 39:1748-1753.

McGuigan, C. (1998) "Synthesis and evaluation of some masked phosphate esters of the anti-herpetic drug 882C (netivudine) as potential antiviral agents" *Antiviral Chem. Chemother.* 9:187-197.

McGuigan, C., et al. (1994) "Certain phosphoramidate derivatives of dideoxy uridine (ddU) are active against HIV and successfully by-pass thymidine kinase" *FEBS Lett.* 351:11-14.

McIntee, E.J., et al. (1997) "Probing the mechanism of action and decomposition of amino acid phosphomonoester amidates of antiviral nucleoside prodrugs" *J. Med. Chem.* 40:3323-3331.

McKay, G.A., et al. (1994) "Broad spectrum aminoglycoside phosphotransferase type III from *Enterococcus*: Overexpression, purification, and substrate specificity" *Biochem* 33:6936-6944.

Meden, H., et al. (1994) "Elevated serum Levels of c-erbB-2 oncogene product in ovarian cancer patients and in pregnancy" *J. Cancer Res. Clin. Oncol.* 120:378-381.

Meier, C., et al. (1997) "ADA-bypass by lipohilic cyclosal-ddAMP pro-nucleotides a second example of the efficiency of the *cyclo*sal-concept" *Bioorg. & Med. Chem. Lett.* 7(12):1577-1582.

Meier, C., et al. (1997) "Cyclic saligenyl phosphotriesters of 2',3'-dideoxy-2',3'-didehydrothymidine (d4T)—a new pro-nucleotide approach[1]" *Bioorg. & Med. Chem. Lett.* 7(2):99-104.

Meier, C., et al. (1997) "*Cyclo*sal-pro-nucleotides: the design and biological evaluation of a new class of lipophilic nucleotide prodrugs" *International Antiviral News* 5(10):183-185.

Melton, R.G., et al. (Feb. 21, 1996) "Antibody-enzyme conjugates for cancer therapy" *J. Natl. Canc. Institute* 88(3/4):153-165.

Mobashery, S., et al (Jun. 15, 1986) "Reactions of *Escherichia coli* TEM β-lactamase with cephalothin and with $C_{10}$-dipeptidyl cephalosporin esters" *J. Biol. Chem.* 261(17):7879-7887.

Mobashery, S., et al. (1986) "Conscripting β-lactamase for use in drug delivery. Synthesis and biological activity of a cephalosporin $C_{10}$-ester of an antibiotic depeptide" *J. Am. Chem. Soc.* 108:1686-1688.

Montfort, W.R., et al. (1997) "Thymidylate synthase: Structure, inhibition, and strained conformations during catalysis" *Pharmacol. Ther.* 76(1-3):29-43.

Montgomery, J.A., et al. (1979) "Phosphonate analogue of 2'-deoxy-5-fluorouridylic acid" *J. Med. Chem.* 22(1):109-111.

Morgan, A.S., et al. (Jun. 15, 1998) "Tumor efficacy and bone marrow-sparing properties of TER286, a cytotoxin acitivated by glutathione S-transferase" *Cancer Res.* 58:2568-2575.

Murakami, Y., et al. (1998) "Accumulation of genetic alterations and their significance in each primary human cancer and cell line" *Mutat. Res.* 400(1-2):421-437.

Naesens, L., et al. (Apr. 1997) "Anti-HIV Activity and Metabolism of Phosphoramidate Derivatives of D4T-MP with Variations in the Amino Acid Moiety" *Poster Session 1, The Tenth International Conference on Antiviral Research*, Hotel Nikko, Atlanta, GA, Apr. 6-11, 1997; published in *Antiviral Research* 34(2):A54 (Abstract 40).

Nakano, T., et al. (1994) "Critical role of phenylalanine 34 of human dihydrofolate reductase in substrate and inhibitor binding and in catalysis" *Biochem.* 33:9945-9952.

Negishi, K., et al. (1996) "Enhancement of *N*4-aminocytidine-induced mutagenesis by Ni++ ion" *Nucl. Acids Symposium* 35:137-138.

Nelson, J. A., et al. (Jun. 1984) "Potentiation of Methotrexate Toxicity by Dipyridamole" *Cancer Res.* 44:2493-2496.

Nooter, K., et al. (1996) "Molecular mechanisms of multidrug resistance in cancer chemotherapy" *Pathol. Res. Pract.* 192:768-780.

Osaki, M., et al. (1997) "5-fluorouracil (5-FU) induced apoptosis in gastric cancer cell lines: Role of the p53 gene" *Apoptosis* 2:221-226.

Oshiro, Y., et al. (1992) "Genotoxic properties of (*E*)-5-(2-bromovinyl)-2'-deoxyuridine (BVDU)" *Fund. Appl. Toxicol.* 18:491-498.

Paradiso, A., et al. (2000) "Thymidilate synthase and p53 primary tumour expression as predictive factors for advanced colorectal cancer patients" *British J. of Cancer* 82(3):560-567.

Pardo, E.G., et al. (1987) "The incorporation of deoxyuridine monophosphate into DNA increases the sister-chromatid exchange yield" *Exp. Cell Res.* 168:507-517.

Park, N.-H., et al. (Jun. 1982) "Chemotherapeutic efficacy of E-5-(-2bromovinyl)-2'-deoxyuridine for orofacial infection with herpes simplex virus type 1 in mice" *J. Infectious Diseases* 145(6):909-913.

Pedersen-Lane, J., et al. (1997) "High-level expression of human thymidylate synthase" *Protein Expression and Purification* 10:256-262.

Pegram, M.D., et al. (1997) "The effect of HER-2/heu overexpression on chemotherapeutic drug sensitivy in human breast and ovarian cancer cells" *Oncogene* 15:537-547.

Perry, K.M., et al. (1990) "Plastic adaptation toward mutations in proteins: Structural comparison of thymidylate synthases" *Proteins* 8:315-333.

Pestalozzi, B.C., et al. (1997) "Prognostic importance of thymidylate synthase expression in early breast cancer" *J. Clin. Oncol.* 15(5):1923-1931.

Peters, G.J., et al. (1995) "Thymidylate synthase and drug resistance" *Eur. J. Cancer* 31A(7/8):1299-1305.

Phelps, M.E., et al. (1980) "Synthesis and biological activity of 5-fluoro-2'-deoxyuridine 5'-phosphorodiamidates" *J. Med. Chem.* 23:1229-1232.

Pluta, J., et al. (1999) "Synthesis and biological properties of 4-hydroxy, 4-thio-5-pyrimidine derivatives" *Boll. Chim. Farm.* 138(1):30-33.

Pupa, S.M., et al. (1993) "The extracellular domain of the c-*erb*B-2 oncoprotein is released from tumor cells by proteolytic cleavage" *Oncogene* 8:2917-2923.

Ramu, N., et al. (1989) "Circumvention of Adriamycin Resistance by Dipyridamole Analogues: A structure-activity relationship Study" *Int. J. Cancer* 43:487-491.

Roberts, D.W. (1966) "An istotopic assay for thymidylate synthetase" *Biochem.* 5(11):3546-3548.

Robins, M.J., et al. (1981) "Nucleic acid related compounds. 31. Smooth and efficient palladium-copper catalyzed coupling of terminal alkynes with 5-iodouracil nucleosides" *Tetrahedron Lett.* 22:421-424.

Robins, M.J., et al. (1982) "Nucleic acid related compounds. 38. Smooth and high-yield iodination and chlorination at C-5 of uracil bases and *p*-toluyl-protected nucleosides" *Can. J. Chem.* 60:554-557.

Robins, M.J., et al. (1983) "Nucleic acid related compounds. 39. Efficient conversion of 5-iodo to 5-alkynyl and derivated 5-substituted uracil bases and nucleosides" *J. Org. Chem.* 48:1854-1862.

Rogulski, K.R., et al. (Jan. 1, 1997) "Glioma cells transduced with an *Escherichia coli* CD/HSV-1 TK fusion gene exhibit enchanced metabolic suicide and radiosensitivity" *Hum. Gene Ther.* 8:73-85.

Romain, S., et al. (1995) "Prognostic value of cytosolic thymidine kinase activity as a marker of proliferation in breast cancer" *Int. J. Cancer* 61:7-12.

Roninson, I.B., et al. (1984) "Amplification of specific DNA sequences correlates with multi-drug resistance in Chinese hamster cells" *Nature* 309:626-628.

Rooney, P. H., et al. (Nov. 15, 1998) "Comparative Genomic Hybridization Analysis of Chromosomal Alterations Induced by the Development of Resistance to Thymidylate Synthase Inhibitors" *Cancer Res.* 58:5042-5045.

Roth, J.A., et al. (1999) "p53 tumor suppressor gene therapy for cancer" *Oncology* 13(10)(5):148-154.

Ruth, J.L., et al. (1978) "C-5 substituted pyrimidine nucleosides. 1. Synthesis of C-5 allyl, propyl, and propenyl uracil and cystosine nucleosides via organopalladium intermediates" *J. Org. Chem.* 43(14):2870-2876.

Saboulard, D., et al. (1999) "Characterization of the activation pathway of phosphoramidate triester prodrugs of stavudine and zidovudine" *Mol. Pharmacol.* 56:693-704.

Santi, D.V. (Feb. 1980) "Perspectives on the design and biochemical pharmacology of inhibitors of thymidylate synthetase" *J. Med. Chem.* 23(2):103-111.

Sastry, J.K., et al. (1992) "Membrane-permeable dideoxyuridine 5'-monophosphate analogue inhibits human immunodeficiency virus infection" *Mol. Pharmacol.* 41:441-445.

Sauter, G., et al. (1993) "Heterogeneity of *erb*B-2 gene amplification in bladder cancer" *Cancer Res.* 53:2199-2203.

Schiffer, C.A., et al. (1995) Crystal structure of human thymidylate synthase: A structural mechanism for guiding substrates into the active site: *Biochem.* 34:16279-16287.

Schimke, R.T. (1988) "Gene amplification in cultured cells" *J. Biol. Chem.* 263(13):5989-5992.

Schmoll, H.-J. (1994) "Colorectal carcinoma: Current problems and future perspectives" *Ann. Oncol.* 5(3):115-121.

Segovia, M. (1994) "*Leishmania* gene amplification: A mechanism of drug resistance" *Annals Tropical Med. Parasitol.* 88(2):123-130.

Shepard, H.M., et al. (1988) "Resistance of tumor cells to tumor necrosis factor" *J. Clin. Immunol.* 8(5):333-341.

Simon, S.M., et al. (Apr. 1994) "Cell biological mechanisms of multidrug resistance in tumors" *PNAS USA* 91:3497-3504.

Singh, J., et al. (1993) "Studies on the preparation and isomeric composition of $^{186}$Re-pentavalent rhenium dimercaptosuccine acid complex" *Nucl. Med. Commun.* 14:197-203.

Slamon, D.J., et al. (1987) "Human breast cancer: Correlation of relapse and survival with amplification of the HER-2/*neu* oncogene" *Science* 235:177-182.

Slamon, D.J., et al. (1989) "Studies of the HER-2/*neu* proto-oncogene in human breast and ovarian cancer" *Science* 244:707-712.

Smith, K.A., et al. (1995) "Regulation and mechanisms of gene amplification" *Phil. Trans. R. Soc. Lond.* 347:49-56.

Snydman, D.R., et al. (1996) "Analysis of trends in antimicrobial resistance patterns among clinical isolates of *Bacteroides fragilis* group species from 1990 to 1994" *Clinical Infectious Diseases* 23(Suppl. 1):S54-S65.

Staschke, K.A., et al. (1994) "The in vitro anti-hepatitis B virus activity of FIAU [1-(2'-deoxy-2'-fluoro-1-β-D-arabinofuranosyl-4-iodo)uracil] is selective, reversible, and determined, at least in part, by the host cell" *Antiviral Res.* 23:45-61.

Stout, T.J., et al. (1999) "Structure-based design of inhibitors specific for bacterial thymidylate synthase" *Biochem.* 38:1607-1617.

Stühlinger, M., et al. (1994) "Clinical therapy and HER-2 oncogene amplification in breast cancer: Chemo-vs radiotherapy" *J. Steriod Biochem. Mol. Biol.* 49(1):39-42.

Sugarman, B.J., et al. (1985) "Recombinant human tumor necrosis factor-α: Effects on proliferation of normal and transformed cells in vitro" *Science* 230(4728):943-945.

Suki, S., et al. (1995) "Risk classification for large cell lymphoma using lactate dehydrogenase, beta-2 microglobulin, and thymidine kinase" *Leukemia and Lymphoma* 18:87-92.

Sukumar, S., et al. (1990) "Specific patterns of oncogene activation in transplacentally induced tumors" *PNAS USA* 87:718-722.

Takeishi, K., et al. (1985) "Nucleotide sequence of a functional cDNA for human thymidylate synthase" *Nucl. Acid Res.* 13(6):2035-2043.

Tannock, I.F. (Dec. 1996) "Treatment of cancer with radiation and drugs" *J. Clin. Oncol.* 14(12):3156-3174.

Teh, B.T., et al. (1999) "Tumor suppressor genes (TSG)" *Anticancer Research* 19:4715-4728.

Tennant, B.C., et al. (1998) "Antiviral activity and toxicity of fialuridine in the woodchuck model of hepatitis B virus infection" *Hepatol.* 28(1):179-191.

Tolstikov, V.V., et al. (1997) "Synthesis and DNA duplex stabilities of oligonucleotides containing C-5-(3-methoxypropynyl)-2'-deoxyuridine residues" *Nucleosides & Nucleotides* 16(3):215-225.

Troutner, D.E. (1987) "Chemical and physical properties of radionuclides" *Nucl. Med. Biol.* 14(3):171-176.

Tsavaris, N., et al. (1990) "Multimodal Biochemical Modulation of 5-Fluorouracil Activity in Advanced Colorectal Cancer with Allopurinol, Folinic Acid and Dipyridamol" *J. Chemother.* 2(2):123-126.

Ubeda, M., et al. (1997) "The large subunit of the DNA replication complex C (DSEB/RF-C140) cleaved and inactivated by caspace-3 (CPP32/YAMA) during fas-induced apoptosis" *J. Biol. Chem.* 272(31):19562-19568.

Valette, G., et al. (1996) "Decomposition pathways and *in vitro* HIV inhibitory effects of isoddA pronucleotides: Toward a rational approach for intracellular delivery of nucleoside 5'-monophosphoates" *J. Med. Chem.* 39:1981-1990.

Van de Vijver, M., et al. (1987) "Amplification of the neu (c-*erB*-2) oncogene in human mammary tumors is relatively frequent and is often accompanied by amplification of the linked c-*erbA* oncogene" *Mol. Cell. Biol.* 7(5):2019-2023.

Volm, M., et al. (1992) "Relationship of inherent resistance to doxorubicin, proliferative activity and expression of P-glycoprotein 170, and glutathione S-transferase-π in human lung tumors" *Cancer* 70(4):764-769.

Wadler, S., et al. (Sep. 1987) "Phase II Trial of Oral Methotrexate and Dipyridamole in Colorectal Carcinoma" *Cancer Treat. Rep.* 71(9):821-824.

Wahba, A.J., et al. (Mar. 1961) "Direct spectrophotometric evidence for the oxidation of tetrahydrofolate during the enzymatic synthesis of thymidylate" *J. Biol. Chem.* 236(3):PC11-PC12.

Wallis, M.P., et al. (1999) "Synthesis and anit-HIV activity of C4-modified pyrimidine nucleosides" *Il Farmaco* 54:83-89.

Wang, S., et al. (1996) "Identification and characterization of Ich-3, a member of the interleukin-1β converting enzyme (ICE)/Ced-3 family and an upstream regulator if ICE" *J. Biol. Chem.* 271(34):20580-20587.

Wataya, Y., et al. (Apr. 1979) "*trans*-5-(3,3,3-trifluoro-1-propenyl)-2'-deoxyuridylate: A mechanism-based inhibitor of thymidylate synthetase" *J. Med. Chem.* 22(4):339-340.

Wettergren, Y., et al. (1994) "Drug-specific rearrangements of chromosome 12 in hydroxyurea-resistance mouse SEWA cells: Support for chromosomal breakage model of gene amplification" *Somatic Cell Mol. Genet.* 20(4):267-285.

Whalen, R., et al. (1998) "Human glutathione S-transferases" *Seminars in Liver Disease* 18(4):345-358.

Willson, J. K.V., et al. (Oct. 1, 1988) "Phase I Clinical Trial of a Combination of Dipyridamole and Acivicin Based Upon Inhibition of Nucleoside Salvage" *Cancer Res.* 48:5585-5590.

Wright, AMP, et al. (2000) "Enhancement of retention and cytotoxicity of 2-chlorodeoxyadenosine in cultured human leukemia lymphoblasts by nitrobenzylthioinosine, an inhibitor of equilibrative nucleoside transport" *Leukemia* 14:52-60.

Yen, Y., et al. (Jul. 15, 1994) "Characterization of a hydroxyurea-resistant human KB cell line with supersensitivity to 6-thioguanine" *Cancer Res.* 54:3686-3691.

Yin, Y., et al. (1992) "Wild-type p53 restores cell cycle control and inhibits gene amplification in cells with mutant p53 alleles" *Cell* 70:937-948.

Zeid, I.F., et al. (1999) "Synthesis of new thiolated acyclonucleosides with potential anti-HBV activity" *Nucleosides & Nucleotides* 18(1):95-111.

Zhou, Q., et al. (1997) "Target protease specificity of the viral serpin CrmA" *J. of Biol. Chem.* 272(12):7797-7800.

Aupperle, K. et al., Regulation of Synoviocyte Proliferation, Apoptosis, and Invasion by the p53 Tumor Suppressor Gene, (Apr. 1998) *American Journal of Pathology*, vol. 152, No. 4.

Zuoning, H et al., Dominant-Negative p53 Mutations in Rheumatoid Arthritis, (1999) Arthritis & Fheumatism 42: No. 6, Jun. pp. 1088-1092.

International Search Report, International application No. PCT/US02/01361, dtd Dec. 16, 2002.

Balzarini et al. "Increased Sensitivity of Thymidine Kinase-Deficient (TK) Tumor Cell Lines to the Cell Growth Inhibitory Effects of (E)-5-(2-Bromovinyl)-2'-Deoxyuridine (BVDU) and Related Compounds" *Anticancer Research* 6:1077-1084 (1986).

Balzarini et al. "Marked Inhibitory Activity of Masked Aryloxy Aminoacyl Phosphoramidate Derivatives of Dideoxynucleoside Analogues Against Visna Virus Infection" *J. of Acquired Immune Deficiency Syndromes and Human Retrovirology* 17:296-302 (1998).

\* cited by examiner

METHODS TO TREAT AUTOIMMUNE AND INFLAMMATORY CONDITIONS

CROSS-REFERENCE TO RELATED APPLICATIONS

This application claims priority under 35 U.S.C. § 119(e) of U.S. Provisional Application No. 60/262,849, filed Jan. 19, 2001, the contents of which are hereby incorporated by reference into the present disclosure.

TECHNICAL FIELD

The present invention is in the field of medicinal chemistry and relates to other areas such as pharmacology and immunology. In particular, it provides methods to treat autoimmune disorders and inflammatory conditions.

BACKGROUND

The function of tumor suppressor genes is a major focus of recent attempts to develop innovative therapeutics for the treatment cancer. The products of tumor suppressor gene expression are generally characterized as negative regulators of cell proliferation (Knudson, A. G. (1993), Weinberg, R. A. (1995)). Thus, therapeutic approaches to date include gene therapies to restore inactive or missing tumor suppressor function in cancer cells to re-establish normal cellular function or induce apoptosis (Clayman, G. L. (2000), Knudson, A. G. (1993)).

Functional loss of tumor suppressor genes also has been linked to hyperproliferative inflammatory or autoimmune diseases that have cellular hyperproliferation as one of their characteristics (Cordan-Cardo, C. and Prives, C. (1999)) and/or defective apoptosis (programmed cell death) (Mountz, J. D. et al. (1994)). These include: rheumatoid arthritis, systemic lupus erythmatosus, psoriatic arthritis, reactive arthritis, Crohn's disease, ulcerative colitis and scleroderma. Table 1 lists literature examples which suggest that such a link may exist.

Wolff, B. and Naumann, M. (1999); DiCiommo et al. (2000)), and alteration in cell-cell interactions (Plath et al. (2000)). Inactivation of tumor suppressor function by somatic mutation or via interaction with virally-encoded proteins is proposed to contribute to the proliferative/inflammatory aspect of athersclerosis, restenosis or other hyperproliferative diseases (Tanaka, K. et al. (1999); Aoki, M. et al. (1999); Guevara, N. V. et al. (1999); Iglesias, M. et al. (1998)). Finally, the expression of the proinflammatory cytokine, macrophage inhibitory factor (MIF), may be capable of inactivating p53 function in some cell types (Hudson, J. D. et al. (1999); Cordon-Cardo, C. and Prives, C. (1999); Portwine, C. (2000)).

DISCLOSURE OF THE INVENTION

This invention provides methods for treating cells or tissue involved in a pathology selected from the group consisting of an autoimmune disease and an inflammatory condition, by contacting the cells or tissue with an effective amount of a compound selected from the group consisting of a 1,5-substituted pyrimidine derivative or analog and furano-pyrimidone derivative or analog. The methods can be practiced in vitro, ex vivo an in vivo. In one aspect, the cells or tissue are characterized by loss of tumor suppressor function. In another aspect, the cells overexpress an endogenous intracellular enzyme such as thymidylate synthase.

When practiced in vivo in a subject, the invention provides a method for treating a subject having an autoimmune disorder or inflammatory condition by delivering to the subject an effective amount of one or more of these compounds. Methods for synthesizing the compounds are described herein and in Applicant's prior patent literature, e.g., PCT/US98/16607 and PCT/US99/01332, which describe the compounds as "ECTA" compounds or prodrugs.

Also provided herein is an assay for selecting agents that inhibit the growth of cells or tissue involved in a pathology selected from the group consisting of an autoimmune disease and an inflammatory condition.

TABLE 1

Literature Examples Suggesting that Biological Expression of TP53 Tumor Suppressor Mutation/Inactivation Relates to Noncancer Hyperproliferative Disease, Autoimmune Disease and Inflammation.

| Impact | Disease Effect | Reference |
|---|---|---|
| Increased IL6 | Proliferation Inflammation Rheumatoid Arthritis | Han et al. (1999) |
| Increased metalloproteinases | Tissue Degradation | Sun, Y. et al. (2000) |
| Increased proliferation of synovial cells | Rheumatoid arthritis | Aupperle, K. R. et al. (1998) |
| Genetic instability and disease progression | Chronic inflammation Ulcerative colitis | Tak. P. P. et al. (2000) Lang, S. M. et al. (1999) |
| Increased expression of E2F regulated genes (TS, DHFR) | Proliferation Drug resistance Multiple autoimmune and inflammatory diseases | Banerjee, D. et al. (1998) |
| Viral proteins expression leading to p53 inactivation | Atherslcerosis | Tanaka, K. et al. (1999) |
| Increased angiogensis | Supports hyper-proliferative States, ex. enabling atheromaorpannus formation. | Zhang, L. et al. (2000) |

Loss of RB/p16 function can result in similar proinflammatory, proliferative and dedifferentiating effects on cells (Carson, R. A. and Haneji, N. (1999); Shim, J. et al. (2000);

The methods are useful to treat or ameliorate the symptoms of autoimmune diseases, for example, systemic lupus erythematosus, rheumatoid arthritis, psoriatic arthritis, reactive arthritis, Sjögren's syndrome, graft-versus-host disease (GVHD), myasthenia gravis, atherosclerosis, glomerulonephritis, Type 1 diabetes, muscular dystrophy and osteoarthritis. The methods are also useful to treat or ameliorate the symptoms associated with an inflammatory condition, for example psoriasis, asthma, ulcerative colitis, scleroderma, inflammatory bowel disease, and Crohn's disease.

MODES FOR CARRYING OUT THE INVENTION

General Techniques

Figure 1:
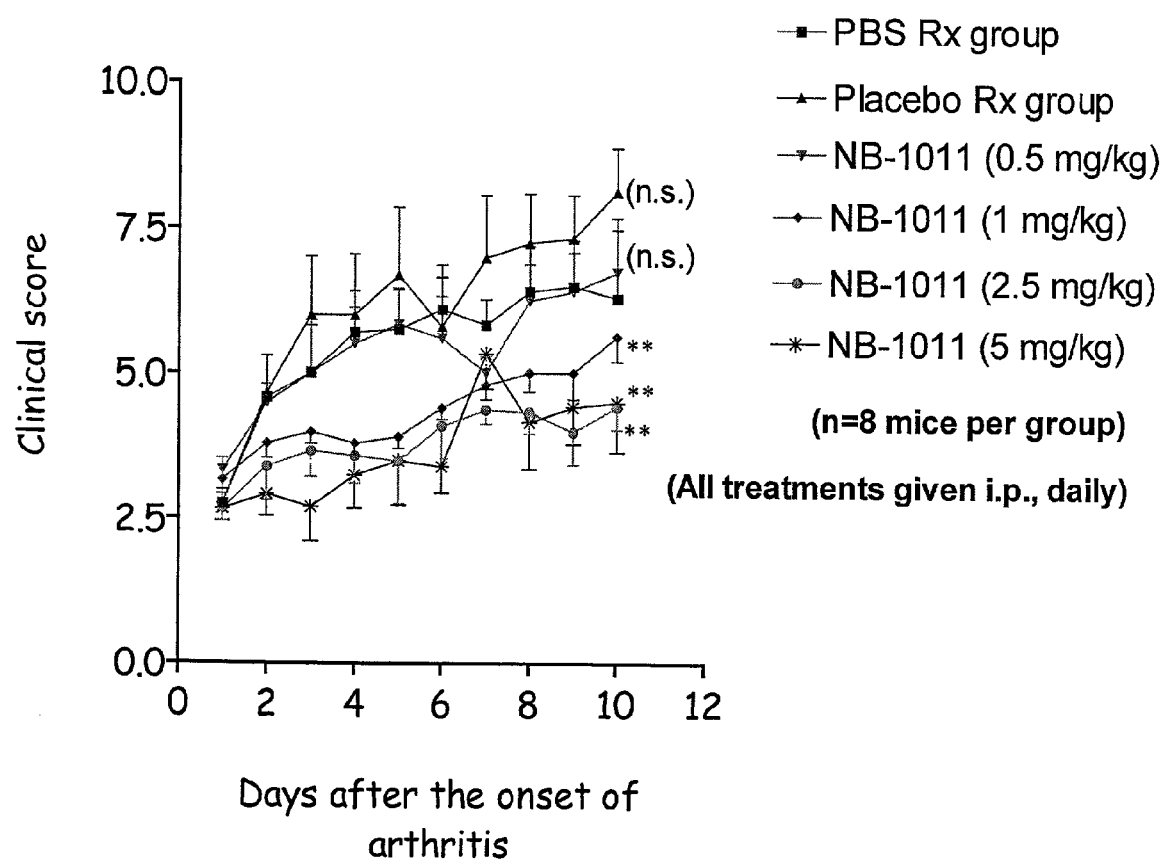
FIG. 1 shows clinical scoring of animals with collagen-induced arthritis using NB 1011, a 5'-phosphoramidatyl deoxyuridine derivate and controls.

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "MOLECULAR CLONING: A LABORATORY MANUAL" Second Edition (Sambrook et al., 1989); "OLIGONUCLEOTIDE SYNTHESIS" (M. J. Gait, ed., 1984); "ANIMAL CELL CULTURE" (R. I. Freshney, ed., 1987); the series "METHODS IN ENZYMOLOGY" (Academic Press, Inc.); "HANDBOOK OF EXPERIMENTAL IMMUNOLOGY" (D. M. Weir & C. C. Blackwell, eds.); "GENE TRANSFER VECTORS FOR MAMMALIAN CELLS" (J. M. Miller & M. P. Calos, eds., 1987); "CURRENT PROTOCOLS IN MOLECULAR BIOLOGY" (F. M. Ausubel et al., eds., 1987, and periodic updates); "PCR: THE POLYMERASE CHAIN REACTION" (Mullis et al., eds., 1994); "CURRENT PROTOCOLS IN IMMUNOLOGY" (J. E. Coligan et al., eds., 1991); and J. March, ADVANCED ORGANIC CHEMISTRY: REACTIONS, MECHANISMS AND STRUCTURE, $4^{th}$ edition (John Wiley & Sons, NY (1992).

Definitions

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "analog" is intended to mean a structural derivative of a compound that differs from it by at least one element. The term "derivative" is intended to mean a compound derived or obtained by another and containing the essential elements of the parent substance.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

A "subject" is a vertebrate, preferably a mammal, more preferably a human. Mammals include, but are not limited to, murines, simians, humans, farm animals, sport animals, and pets.

An "effective amount" is an amount sufficient to effect beneficial or desired results. For example, a therapeutic amount is one that achieves the desired therapeutic effect. This amount may be the same or different from a prophylatically effective amount, which is an amount necessary to prevent onset of disease or disease symptoms. An effective amount can be administered in one or more administrations, applications or dosages.

An "autoimmune disorder" is any condition in which an organism produces antibodies or immune cells which recognize the organism's own molecules, cells or tissues. Non-limiting examples of autoimmune disorders include rheumatoid arthritis, Sjögren's syndrome, graft versus host disease, myasthenia gravis, and systemic lupus erythematosus.

An "inflammatory condition" shall mean those conditions that are characterized by a persistent inflammatory response with pathologic sequelae. This state is characterized by infiltration of mononuclear cells, proliferation of fibroblasts and small blood vessels, increased connective tissue, and tissue destruction. Chronic inflammatory diseases include Crohn's disease, psoriasis, and asthma, are also included within the term "inflammatory condition." Autoimmune diseases such as rheumatoid arthritis and systemic lupus erythematosus can also result in a chronic inflammatory state.

As used herein, to "treat" includes systemic amelioration of the symptoms associated with the pathology and/or a delay in onset of symptons. Clinical and sub-clinical evidence of "treatment" will vary with the pathology, the individual and the treatment. For example, administration for the treatment of arthritic conditions can result in decreased blood vessel formation in cartilage, specifically joints, resulting in increased mobility and flexibility in these regions. For the treatment of psoriasis, administration will reduce dermatological symptoms such as scabbing, flaking and visible blood vessels under the surface of the skin.

In vitro treatment includes induction of apoptosis, as well as clinical (histological) and sub-clinical (e.g., biochemical and genetic changes associated with a reversal or dimunition of the pathological state.) Clinical and sub-clinical evidence of "treatment" will vary with pathology, the individual or subject, the cell or tissue type and the treatment.

"An endogenous intracellular enzyme" is one that is expressed by the cell whose regulation or expression can vary. In one aspect, the enzyme selectively activates a compound whose product inhibits proliferation of the cells or kills them. In one aspect, the enzyme is overexpressed in a diseased cell as compared to a normal healthy cell. An example of such is thymidylate synthase (TS).

A "composition" is intended to mean a combination of active agent and another compound or composition, inert (for example, a solid support, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARMACEUTICAL SCIENCES, 15th Ed., Mack Publ. Co., Easton, Pa. (1975).

Methods of Treatment

Autoimmune diseases and inflammatory conditions are treated by contacting the cells or tissue associated with these pathologies with an effective amount of a compound selected from the group consisting of a 1,5-substituted pyrimidine derivative or analog and furano-pyrimidone derivative or analog.

When practiced in a subject other than a human patient such as a mouse, the method provides an animal model for use in discovering alternative agents and therapies. In a human patient, the method treats an autoimmune disorder or inflammatory condition. Methods for detecting clinical and sub-clinical evidence of effective therapy are known in the art. In each of these methods, an effective amount of a compound selected from the group consisting of a 1,5-substituted pyrimidine derivative or analog and furano-pyrimidone derivative or analog, is delivered or administered to the subject, e.g., mouse or human patient.

Numerous compounds of the class defined as a 1,5-substituted pyrimidine derivative or analog and furano-pyrimidone derivative or analog are useful in the invention methods. The 1,5-substituted pyrimidine derivative or analog is substituted at the 5-position with a group that is extractable from pyrimidine by the endogenous, intracellular enzyme, wherein the substituent at the 1-position is selected from the group consisting of substituted sugar, unsubstituted sugar, substituted thio-sugar, unsubstituted thio-sugar, substituted carbocyclic, unsubstituted carbocyclic, substituted acyclic and unsubstituted acyclic. The 1,5-substituted pyrimidine derivative or analog includes, but is not limited to, a 5'-phosphoryl, 5-substituted deoxyuridine derivative or analog or a 5'-phosphoramidate, 5-substituted deoxyuridine derivative or analog. More specifically, the 1,5-substituted pyrimidine derivative or analog includes, but is not limited to, (E)-5-(2-bromovinyl)-2'-deoxy-5'-uridyl phenyl L-alanylphosphoramidate. These compounds and methods to prepare them are provided herein.

In one aspect, the disease is an autoimmune disease, for example, psoriatic arthritis, atherosclerosis, reactive arthritis, systemic lupus erythematosus, rheumatoid arthritis, Sjögren's syndrome, graft-versus-host disease, osteoarthritis, glomerulonephritis, Type 1 diabetes, muscular dystrophy, or myasthenia gravis. In another aspect, the disease is an inflammatory condition, for example, psoriasis, asthma, ulcerative colitis, inflammatory bowel disease, scleroderma or Crohn's disease.

Co-Administration

Co-administration of these compounds with other agents may provide unexpected synergistic therapeutic benefit. In the co-administration methods, the compounds are also useful in reducing deleterious side-effects of known therapies and therapeutic agents, as well as yet to be discovered therapies and therapeutic agents. Agents or drugs that neutralize or prevent the production of tumor necrosis factor-α (TNF-α) such as an anti-TNF-α antibody or soluble TNF-α receptor are examples of agents for co-administration with the compounds. Additional examples include, but are not limited to corticosteriods, non-steroidal anti-inflammatory drugs (N-SAIDS), and anti-rheumatic drugs.

The use of operative combinations is contemplated to provide therapeutic combinations that may lower total dosage of each component than may be required when each individual therapeutic method, compound or drug is used alone. A reduction in adverse effects may also be noted. Thus, the present invention also includes methods involving co-administration of the compounds described herein with one or more additional active agents or methods. Indeed, it is a further aspect of this invention to provide methods for enhancing other therapies and/or pharmaceutical compositions by co-administering a compound of this invention. In co-administration procedures, the agents may be administered concurrently or sequentially. In one embodiment, the compounds described herein are administered prior to the other active agent(s), therapy or therapies. The pharmaceutical formulations and modes of administration may be any of those described herein or known to those of skill in the art.

Use of Compounds for Preparing Medicaments

The compounds of the present invention are also useful in the preparation of medicaments to treat a variety of autoimmune diseases or inflammatory conditions. The methods and techniques for preparing medicaments of a compound are known in the art. For the purpose of illustration only, pharmaceutical formulations and routes of delivery are detailed below.

Thus, one of skill in the art would readily appreciate that any one or more of the compounds described more fully below, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

Pharmaceutical Delivery

Various delivery systems are known and can be used to administer a compound or an agent of the invention, e.g., encapsulation in liposomes, microparticles, microcapsules, receptor-mediated endocytosis and the like. Methods of delivery include but are not limited to, intra-arterial, intramuscular, intravenous, intranasal, and oral routes. In a specific embodiment, it may be desirable to administer the pharmaceutical compositions locally to the area in need of treatment; this may be achieved by, for example and not by way of limitation, local infusion during surgery, by injection, or by means of a catheter. To determine patients that can be beneficially treated, a tissue sample can be removed from the patient and the cells are assayed for sensitivity to the agent.

Therapeutic amounts can be empirically determined and will vary with the pathology being treated, the subject being treated and the efficacy and toxicity of the compound as well as whether the compound is used alone or in combination with other agents of therapeutic methods. When delivered to an animal, the method is useful to further confirm efficacy of the agent. One example of an animal model is MLR/MpJ-lpr/lpr ("MLR-lpr") (available from Jackson Laboratories, Bal Harbor, Me.). MLR-lpr mice develop systemic autoimmune disease.

Administration in vivo can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician.

Suitable dosage formulations and methods of administering the agents can be readily determined by those of skill in the art. For example, the compounds are administered at about 0.01 mg/kg to about 200 mg/kg, alternatively at about 0.1 mg/kg to about 100 mg/kg, or alternatively at about 0.5 mg/kg to about 50 mg/kg. When the compounds described herein are co-administered with another agent (e.g., as sensitizing agents) or therapy, the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parenteral (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue.

Screening Assays

This invention also provides a quick and simple screening assay to enable initial identification of novel compounds and combinations useful to treat or ameliorate symptoms of autoimmune and/or chronic inflammatory conditions.

In one aspect, the assay requires contacting a first sample comprising suitable cells or tissue ("control sample") with an effective amount of a compound selected from the group consisting of a deoxyuridine, a substituted deoxyuridine, a substituted deoxyuridine derivative and analogs thereof and contacting a second sample of the suitable cells or tissue ("test sample") with the agent to be assayed. In a further aspect, the test agent is contacted with a third sample of cells or tissue comprising normal counterpart cells or tissue to the control and test samples and selecting agents that treat the second sample of cells or tissue but does not adversely effect the third sample. For the purpose of the assays described herein a suitable cell or tissue is one involved in pathogenesis of autoimmune or chronic inflammatory conditions. Examples include, but are not limited to synovial fluid, a chondrocyte or an immune cell, such as a T cell, a macrophage, and an NK cell.

In a further aspect, the cells are tissue are characterized by the loss of a native tumor suppressor function.

In yet a further aspect, the assay requires at least two cell types, the first being a suitable control cell. The second cell type is of the same type or tissue as the control cell but differs in that pathogenesis toward disease has begun. In one aspect, pathogenesis is determined enzymatically by noting enhanced or over expression of an endogenous intracellular enzyme that activates the compound into a toxic entity. For example, the compound or agent to be tested can be activated by an endogenous intracellular enzyme that is overexpressed or differentially expressed in a pathological cell as compared to its normal counterpart. An example of such an enzyme includes, but is not limited to thymidylate synthase. Alternatively, a cell genetically modified to differentially express the enzyme or enzymes (containing the appropriate species of enzyme) can be used. Transfection of host cells with polynucleotides encoding the enzyme can be either transient or permanent using procedures well known in the art and described by Chen, L. et al. (1996), Hudziak, R. M. et al. (1988), or Carter, P. et al. (1992), and in the experimental section below. The cells can be procaryotic (bacterial such as *E. coli*) or eucaryotic. The cells can be mammalian or non-mammalian cells, e.g., mouse cells, rat cells, human cells, fungi (e.g., yeast) or parasites (e.g., *Pneumocystis* or *Leishmania*) which cause disease.

Suitable vectors for insertion of the cDNA are commercially available from Stratagene, La Jolla, Calif. and other vendors. The amount of expression can be regulated by the number of copies of the expression cassette introduced into the cell or by varying promoter usage. The level of expression of enzyme in each transfected cell line can be monitored by immunoblot and enzyme assay in cell lysates, using monoclonal or polyclonal antibody previously raised against the enzyme for immuno-detection. (Chen, L. et al. (1996)). Enzymatic assays to detect the amount of expressed enzyme also can be performed as reviewed by Carreras, C. W. and Santi, D. V. (1995), or the method described in the experimental section below.

In a further aspect, more than one species of enzyme can be used to separately transduce separate host cells, so that the effect of the candidate drug with an enzyme can be simultaneously compared to its effect on another enzyme or a corresponding enzyme from another species.

The compositions can be directly added to the cell culture media and the target cell or the culture media is then assayed for the amount of label released from the candidate prodrug if the prodrug contains a detectable label. Alternatively, cellular uptake may be enhanced by packaging the prodrug into liposomes using the method described in Lasic, D. D. (1996) or combined with cytofectins as described in Lewis, J. G. et al. (1996).

The assays are useful to predict whether a subject will be suitably treated by this invention by delivering a compound or composition to a sample containing the cell to be treated and assaying for treatment which will vary with the pathology. In one aspect, the cell or tissue is obtained from the subject or patient by biopsy. Applicants provide kits for determining whether a pathological cell or a patient will be suitably treated by this therapy by providing at least one composition of this invention and instructions for use.

Kits

Applicants also provide kits for determining whether a pathological cell, tissue or patient will be suitably treated by this therapy. Additionally, kits for performance of the assays are provided. These kits contain at least one composition of this invention and instructions for use.

The Compounds

Therapeutic compounds for use in the methods of this invention are one or more selected from the group consisting a 1,5-substituted pyrimidine derivative or analog and a substituted furano-pyrimidone derivative or analog. In one aspect, the 1,5-substituted pyrimidine derivative or analog is substituted at the 5-position with a group that is extractable from pyrimidine by an endogenous, intracellular enzyme. The substituent at the 1-position is selected from the group consisting of substituted sugar, unsubstituted sugar, substituted thio-sugar, unsubstituted thio-sugar, substituted carbocyclic, unsubstituted carbocyclic, substituted acyclic and unsubstituted acyclic. The 1,5-substituted pyrimidine derivative or analog includes, but is not limited to, a 5'-phosphoryl, 5-substituted deoxyuridine derivative or analog or a 5'-phosphoramidate, 5-substituted deoxyuridine derivative or analog. More specifically, the 1,5-substituted pyrimidine derivative or analog includes, but is not limited to, (E)-5-(2-bromovinyl)-2'-deoxy-5'-uridyl phenyl L-alanylphosphoramidate.

In a further embodiment, the compounds are not chemically related to pyrimidines or folates, and can be synthesized based upon known parameters of rational drug design. See Dunn, W. J. et al. (1996).

Compounds useful in the methods of this invention can be described as the L and D isomers of compounds having one of the following structures:

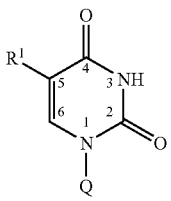

Formula A

Formulae B

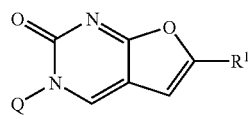

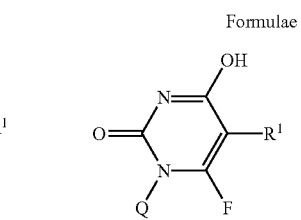

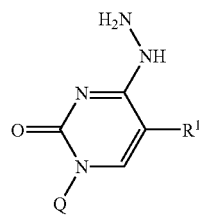

or

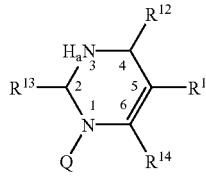

Formula C or tautomers thereof, wherein in Formula C, $R^{12}$ or $R^{13}$ may be the same or different and are selected from the group consisting of oxo, OH or $NHNH_2$, wherein a is 0 or 1, providing that if a is 0 and $R^{13}$ is oxo, then a double bond exits between position 3 and 4 and $R^{12}$ is $NHNH_2$; further providing that if a is 0 and $R^{12}$ is oxo, then a double bond exists between position 2 and 3 and $R^{13}$ is $NHNH_2$; further providing that if a is 1, then $R^{12}$ and $R^{13}$ are both oxo.

While not wishing to be bound by any theory, in one aspect of the above formulae (A, B and C), $R^1$ (at the 5-position) is or contains a leaving group which is a chemical entity that has a molecular dimension and electrophilicity compatible with extraction from the pyrimidine ring by an endogenous, intracellular enzyme (e.g., thymidylate synthase). An embodiment for the substituent in the $R^1$ position is one that could undergo an allylic interchange.

Alternatively, in the above formulae (A, B or C), $R^1$ can be a moiety of the formula:

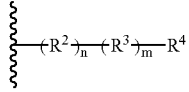

Formula D wherein, $R^4$ is a toxophore.

In one aspect of Formula D, $R^2$ is or contains a divalent electron conduit moiety. In one embodiment, $R^2$ is or contains a mono- or polyunsaturated electron conduit acting to conduct electrons away from the pyrimidine ring and toward $R^4$. In one embodiment, $R^2$ is selected from the group consisting of an unsaturated hydrocarbyl group, an aromatic hydrocarbyl group comprising one or more unsaturated hydrocarbyl groups, and a heteroaromatic group comprising one or more unsaturated hydrocarbyl groups.

Annother example is an alkenyl group of the formula, i.e., $(-CH=CH)_n-R^4$, wherein n is 0 or an integer from 1 to 10, and $R^4$ is a halogen such as I or Br, CN or mercury, or alternatively, $R^1$ is or contains a group selected from hydrogen, alkyl, alkene, alkyne, hydroxy, —O-alkyl, —O-aryl, O-heteroaryl, —S-alkyl, —S-aryl, a cyanide, cyanate, thiocyanate halovinyl group, halomercuric group, —S-heteroaryl, —$NH_2$, —NH-alkyl, —$N(alkyl)_2$, —NHCHO, —NHOH, —NHO-alkyl, $NH_2CONHO$—, and $NHNH_2$. For example, when n is 0 or an integer from 1 to 10, $R^4$ is —$CH_2$—O-A, wherein A is a phosphoramide derivative, or a compound of the formula:

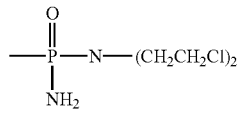

In a yet further aspect, m is 0 and $R^2$ is selected from the group consisting of:

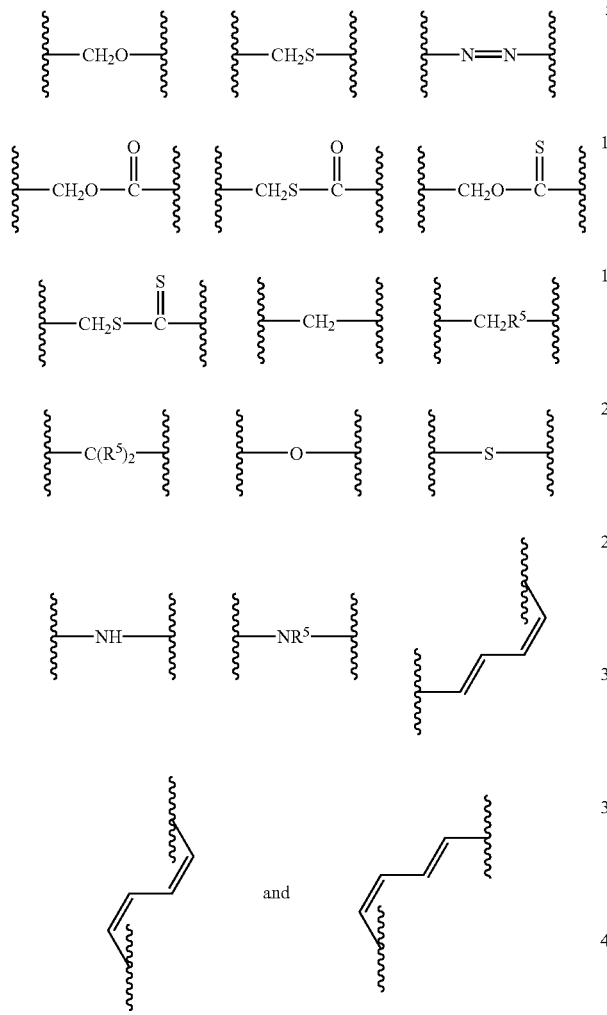

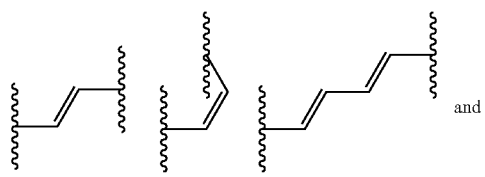

wherein $R^5$ is independently the same or different and is selected from the group consisting of a linear or branched alkyl group having from 1 to 10 carbon atoms, a cycloalkyl group having from 3 to 10 carbon atoms, CN and a halogen.

In one embodiment of Formula D, $R^2$ is an unsaturated hydrocarbyl group having a structure selected from the group consisting of:

In another embodiment of Formula D, $R^2$ is an aromatic hydrocarbyl group having a structure selected from the group consisting of:

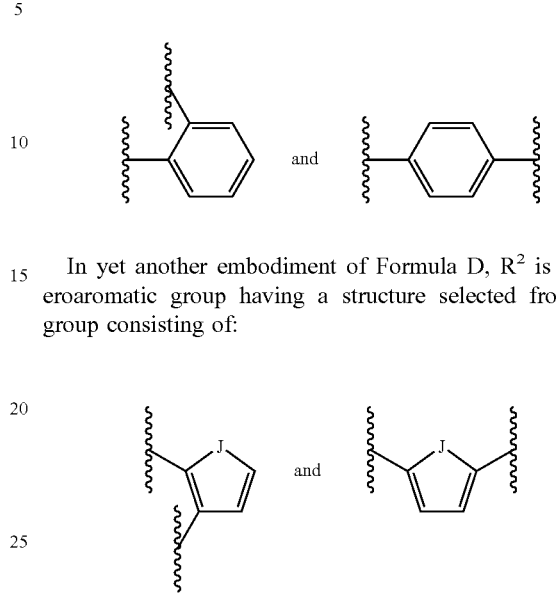

In yet another embodiment of Formula D, $R^2$ is a heteroaromatic group having a structure selected from the group consisting of:

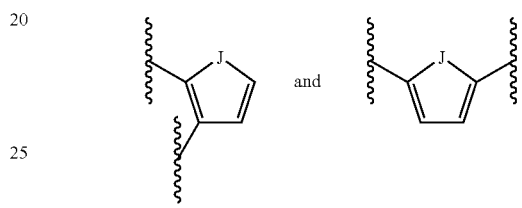

wherein J is a heteroatom, such as —O—, —S—, or —Se—, or a heteroatom group, such as —NH— or —NR$^{ALK}$-, where R$^{ALK}$ is a linear or branched alkyl having 1 to 10 carbon atoms or a cycloalkyl group having 3 to 10 carbon atoms.

In an alternative embodiment of Formula D, $R^3$ is a divalent spacer moiety, also referred to as a spacer unit. Divalent spacers include, but are not limited to, a moiety having a structure:

Formulae E

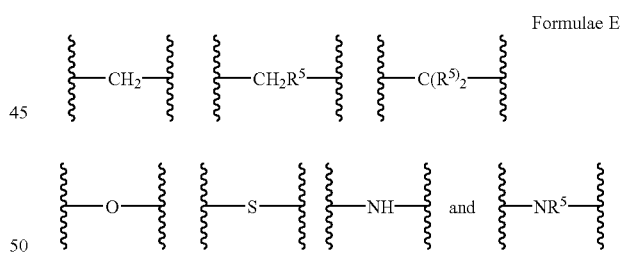

wherein $R^5$ is the same or different and is independently a linear or branched alkyl group having from 1 to 10 carbon atoms, or a cycloalkyl group having from 3 to 10 carbon atoms.

In an alternative aspect of Formula D, $R^3$ is a divalent spacer moiety having a structure selected from the group consisting of:

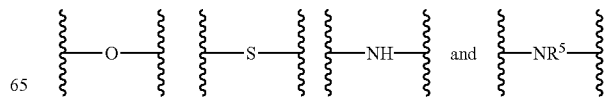

In yet another aspect of Formula D, $R^2$ and $R^3$, taken together form a structure selected from the group consisting of:

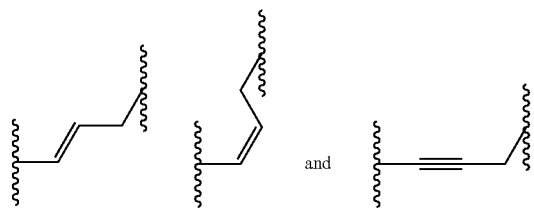

In one embodiment, $R^4$ ($R^4$ in Formula D or $R^1$ in Formulae A, B or C) is or contains a leaving group that is activated or released by an intracellular enzyme. In one embodiment, $R^4$ is or contains a group having a structure selected from the group consisting of F, Cl, Br, I, CN, $SO_3H$, $CO_2H$, $CO_2CH_2CH_3$, $CO_2CH_3$, $SI(CH_3)_3$, CHO, $NO_2$, $CF_3$, $CCl_3$, $CH=C(R^{15})_2$ and a derivative of cisplatin, such as:

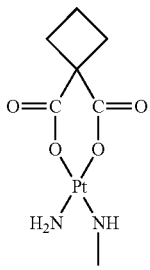

or a substituent selected from the structures:

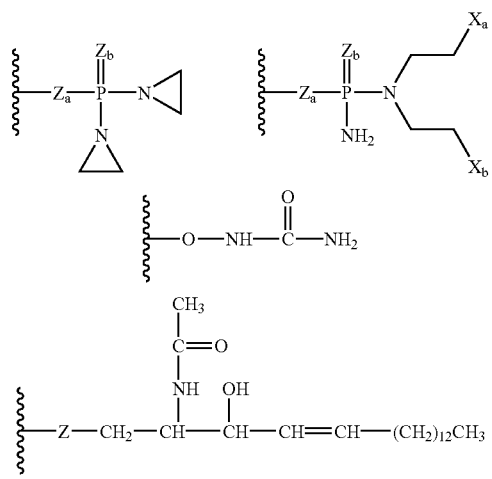

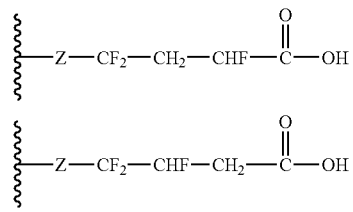

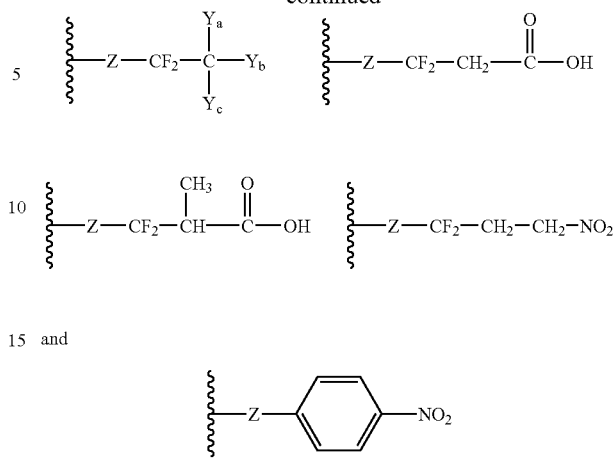

wherein $X_a$, and $X_b$ are independently the same or different and are selected from the group consisting of Cl, Br, I, and a potent leaving group and wherein $Y_a$, $Y_b$ or $Y_c$ are independently the same or different and are hydrogen or F and wherein Z, $Z_a$ and $Z_b$ are independently the same or different and are selected from the group consisting of O and S; and with respect to Formula C, $R^{14}$ is hydrogen or F, providing if $R^{14}$ is F, then a is 1 and $R^{12}$ and $R^{13}$ are both oxo.

In a further aspect, Q is a sugar group, a thio-sugar group, a carbocyclic group or an acyclic carbon group as well as 5'-phosphoryl or phosphoramidate derivatives thereof. Examples of sugar groups include, but are not limited to, monosaccharide cyclic sugar groups such as those derived from oxetanes (4-membered ring sugars), furanoses (5-membered ring sugars), and pyranoses (6-membered ring sugars). Examples of furanoses include threo-furanosyl (from threose, a four-carbon sugar); erythro-furanosyl (from erythrose, a four-carbon sugar); ribo-furanosyl (from ribose, a five-carbon sugar); ara-furanosyl (also often referred to as arabino-furanosyl; from arabinose, a five-carbon sugar); xylo-furanosyl (from xylose, a five-carbon sugar); and lyxo-furanosyl (from lyxose, a five-carbon sugar). Examples of sugar group derivatives include "deoxy", "keto", and "dehydro" derivatives as well as substituted derivatives. Examples of thio sugar groups include the sulfur analogs of the above sugar groups, in which the ring oxygen has been replaced with a sulfur atom. Similar substitutions can be made to the acyclic carbon group. Examples of carbocyclic groups include $C_4$ carbocyclic groups, $C_5$ carbocyclic groups, and $C_6$ carbocyclic groups which may further have one or more substituents, such as —OH groups.

In one embodiment, Q is selected from the group consisting of:

Formulae F

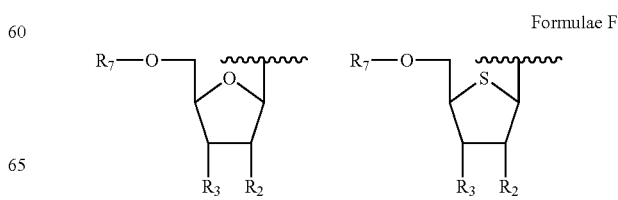

-continued

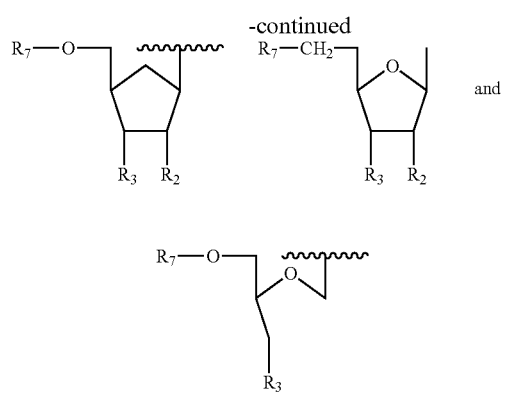

In the above Formula F, $R_2$ and $R_3$ are independently the same or different and are selected from the group consisting of Br, Cl, F, I, H, OH, OC(=O)CH$_3$, —O— and —O-Rg, wherein Rg is a hydroxyl protecting group other than acetyl. $R_7$ is attached to Q at the 5' position of Q and is selected from the group consisting of a hydrogen, a hydroxyl, a phosphate group, a phosphodiester group or a phosphoramidate group. $R_7$ is selected from the group consisting of a hydrogen, a masked phosphate, a phosphoramidate, and derivatives thereof, and wherein $R_2$ and $R_3$ are the same or different and are independently hydrogen, —OH —OC(=O)CH$_3$, or —O—Rg wherein Rg is a hydroxyl protecting group other than acetyl. Any of the members of Formulae F may be in any enantiomeric, diasteriomeric, or stereoisomeric form, including D-form, L-form, α-anomeric form, and β-anomeric form.

In a specific embodiment, Q has the formula:

Formula G

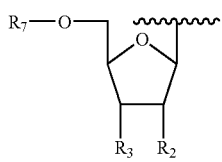

wherein $R_2$ and $R_3$ are independently the same or different and are independently H, —OH, —OC(=O)CH$^3$, or —O-Rg, wherein Rg is a hydroxyl protecting group other than acetyl.

In a further specific embodiment, Q has the following structure:

Formula H

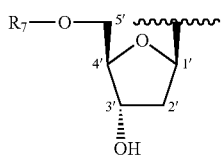

In each of Formulae F, G, or H, $R_7$ is selected from the group consisting of hydrogen, a masked phosphate or a phosphoramidate and derivatives thereof, and wherein $R_2$ and $R_3$ are the same or different and are independently hydrogen or —OH. Alternatively, $R_7$ is a phosphoramidate group derived from an amino acid, including, for example, the twenty naturally occurring amino acids, e.g., alanine and tryptophane. Examples of such include, but are not limited to:

Formula I

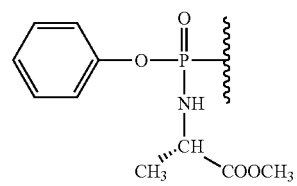

Formula I and its method for preparation, are described in McGuigan, C. et al. (1993), and McGuigan, C. et al. (1996). Additional examples of 5' substituents are:

Formula J

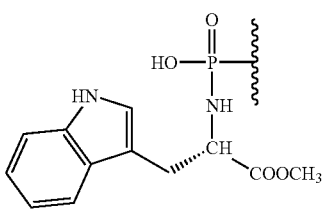

Formula K

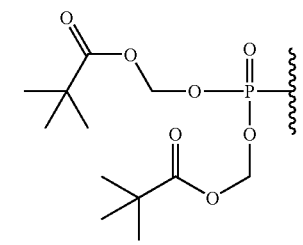

Formula L

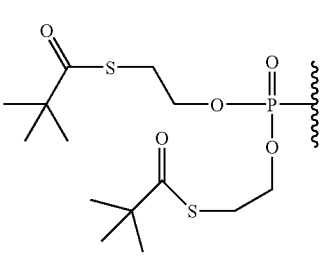

Formula M

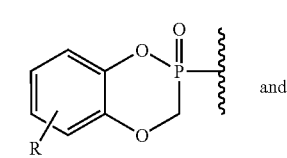
and

Formula N

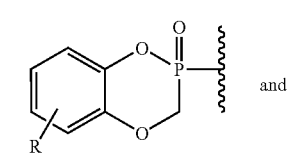

The group identified herein as Formula J, and methods for its preparation, are described in Abraham et al. (1996). Formula K and its method for preparation are described in Freed et al. (1989); Sastry et al. (1992); Farquhar, J. et al. (1994), and Farquhar, J. et al. (1995). Formula L and its method for preparation are described in Valette et al. (1996);

and Benzaria et al. (1996). Formula M and its method of preparation are described in Meier et al. (1997); Meier et al. (1997); and Meier et al. (1997). Formula N and its method for preparation, are described in Hostetler et al. (1997); and Hostetler et al., published International Patent Application No. WO 96/40088 (1996).

In one embodiment, the $R_7$ forms a cyclic group within Q. One such embodiment, and a method for its preparation, is shown below (where DMTr is 4,4'-dimethoxytrityl, Boc is t-butyloxycarbonyl, DCC is 1,3-dicyclohexylcarbodiimide, and 4-DMAP is 4-dimethylaminopyridine):

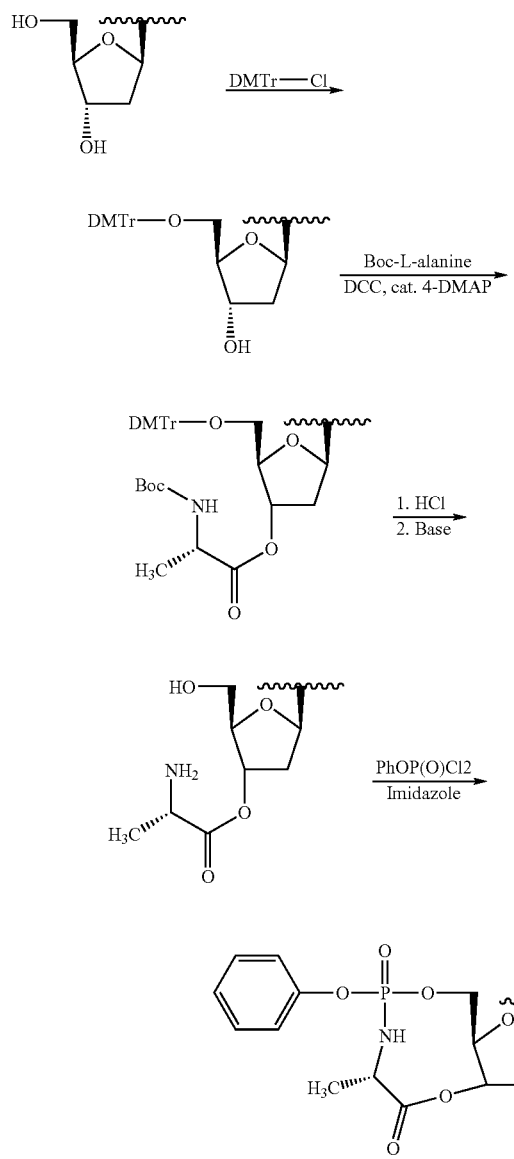

In one embodiment, the compound may be in any enantiomeric, diasteriomeric, or stereoisomeric form, including, D-form, L-form, α-anomeric form, and β-anomeric forms. In an alternative embodiment, the compound may be in a salt form, or in a protected or prodrug form, or a combination thereof, for example, as a salt, an ether, or an ester.

Specific compounds having the L or D structures are shown in Table I, below. Compounds are identified by structure and a numerical designation.

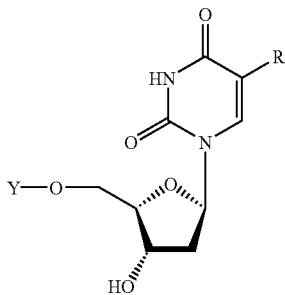

| R | Y = (phenyl-O-P(=O)(NH-CH(CH₃)-CO₂Me)) | Y=H |
|---|---|---|
| –CH=CH–Br | NB 1011 | NB 1015 (BVdU) |
| –CH=C(Br)₂ | NB 1012 | — |
| –CH=CH–Cl | NB 1013 | NB 1020 |
| –CF₃ | NB 1014 | NB 1027 |
| –CH=CH–CH=CH–CO₂CH₂CH₃ | NB 1016 | NB 1021 |
| –CH=CH–CH=CH–Br | NB 1017 | NB 1024 |
| –C≡C–SiMe₃ | NB 1018 | NB 1022 |
| –C≡C–H | NB 1019 | NB 1023 |
| –C≡C–C₈H₁₇ | — | — |
| –C₈H₁₇ | — | — |

The structures of specific examples of compounds useful in the methods of this invention are provided below.

For example, a compound having the structure:

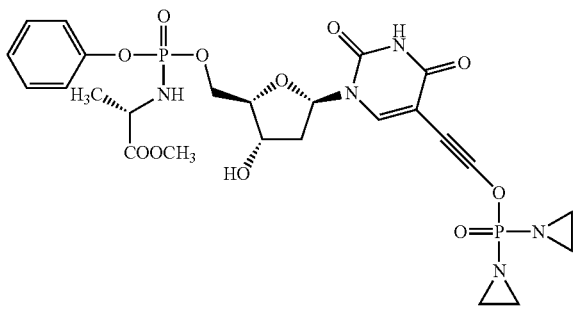

or the nucleoside analog thereof.

A compound having the structure:

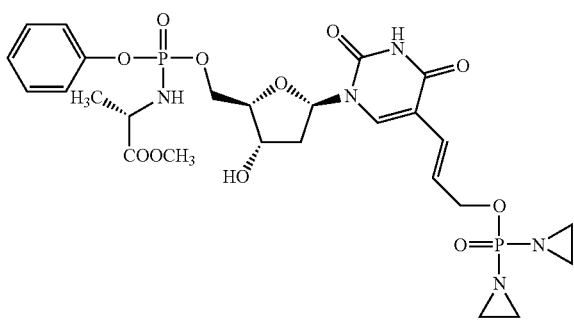

or the nucleoside analog thereof.

A compound having the structure:

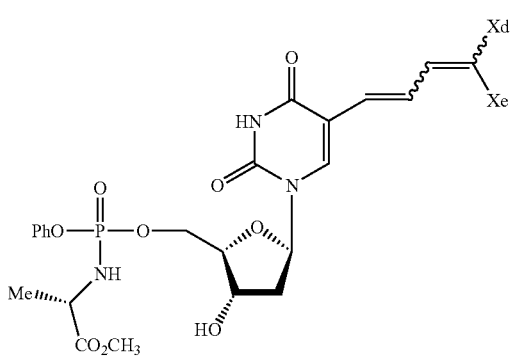

wherein $X_d$ and $X_e$ are independently the same or different and are selected from the group consisting of Cl, Br, I, and CN or the nucleoside analogs thereof. In a more preferred aspect, $X_d$ is Cl or Br and $X_e$ is hydrogen.

A compound having the structure:

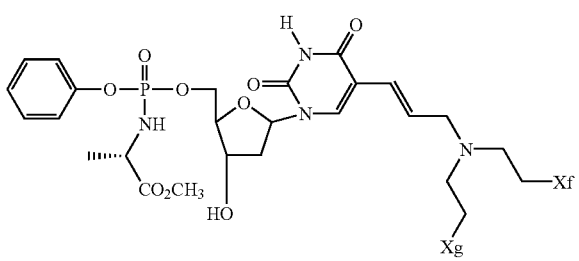

wherein $X_f$ and $X_g$ are independently the same or different and are selected from the group consisting of Cl, Br, I, and CN, or the nucleoside analogs thereof. In a preferred embodiment, $X_f$ and $X_g$ are the same and are each is Cl or Br.

A compound having the structure of the formula:

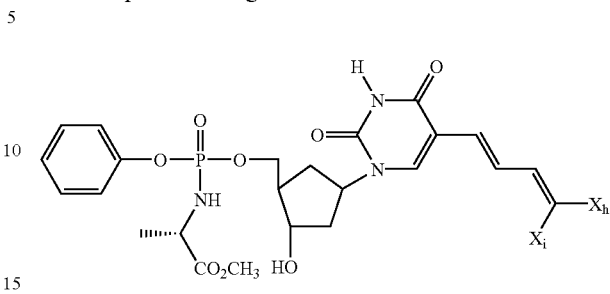

wherein $X_h$ and $X_i$ are independently the same or different and are selected from the group consisting of Cl, Br, I, and CN, or the nucleoside analogs thereof. In a preferred embodiment, $X_h$ and $X_i$ are independently the same or different and are Cl or Br and in a more preferred embodiment, $X_h$ and $X_i$ are both Br.

A compound having the structure:

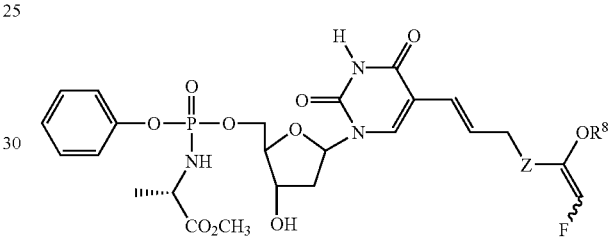

wherein $R^8$ is a lower straight or branched chain alkyl, or the nucleoside analogs thereof.

A compound having the structure:

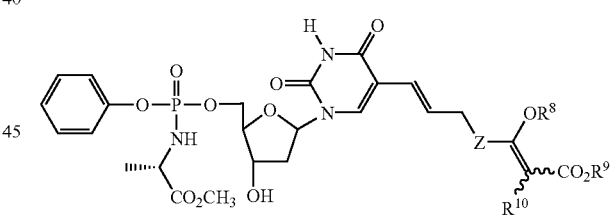

wherein $R^8$ and $R^9$ are lower straight or branched chain alkyls and $R^{10}$ is hydrogen or $CH_3$, or the nucleoside analogs thereof.

A compound having the structure:

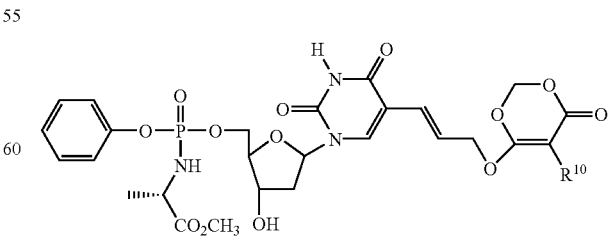

wherein $R^{10}$ is hydrogen or $CH_3$, or the nucleoside analogs thereof.

A compound having the structure:

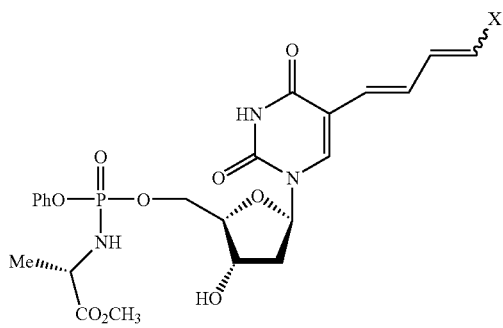

wherein X is selected from the group consisting of $CO_2Et$, Cl, and Br; or the nucleoside analogs thereof.

In a separate embodiment, the above structures are further modified to possess thiophosphodiaziridine instead of phosphodiaziridine groups, using the methods described below.

The compounds can be combined with a carrier, such as a pharmaceutically acceptable carrier, for use in vitro and in vivo. In one embodiment, the compound is in a salt form, or in a protected or prodrug form, or a combination thereof, for example, as a salt, an ether, or an ester.

"Pharmaceutically acceptable salt, prodrug or derivative" as used herein, relates to any pharmaceutically acceptable salt, ester, ether, salt of an ester, solvate, such as ethanolate, or other derivative of a compound of the present invention which, upon administration to a recipient, is capable of providing (directly or indirectly in the case of a prodrug) a compound of this invention or an active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system).

Salts of the prodrugs of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, can be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the prodrugs or compounds identified by the method of this invention include carboxylic acid esters (i.e., —O—C(=O)R) obtained by esterification of the 2'-, 3'- and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-($C_{6-24}$)acyl glycerol. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Examples of lyxo-furanosyl prodrug derivatives of the present invention include, for example, those with chemically protected hydroxyl groups (e.g., with O-acetyl groups), such as 2'-O-acetyl-lyxo-furanosyl; 3'-O-acetyl-lyxo-furanosyl; 5'-O-acetyl-lyxo-furanosyl; 2',3'-di-O-acetyl-lyxo-furanosyl and 2',3',5'-tri-O-acetyl-lyxo-furanosyl.

Ethers of the compounds of the present invention include methyl, ethyl, propyl, butyl, isobutyl, and sec-butyl ethers.

Formulations for in vivo Administration

While it is possible for the composition ingredient to be administered alone, it is preferable to present it as a pharmaceutical formulation comprising at least one active ingredient, as defined above, together with one or more pharmaceutically acceptable carriers therefore and optionally other therapeutic agents. Each carrier must be "acceptable" in the sense of being compatible with the other ingredients of the formulation and not injurious to the patient.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For diseases of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the composition may be employed with either a paraffinic or a water-miscible ointment base. Alternatively, the ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound that enhances absorption or penetration of the ingredients through the skin or other affected areas. Examples of such dermal penetration enhancers include dimethylsulfoxide and related analogs.

The oily phase of the emulsions of this invention may be constituted from known ingredients in a known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the ingredients. The ingredients are preferably present in such formulation in a concentration of about 0.5 to about 20%, advantageously about 0.5 to about 10%, particularly about 1.5% w/w.

Formulations for rectal administration may be presented as a suppository with a suitable base comprising, for example, cocoa butter or a salicylate.

Formulations suitable for vaginal administration may be presented as suppositories, tampons, creams, gels, pastes, foams or spray formulations containing in addition to the ingredients, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the ingredients.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Compositions of the formula of the present invention may also be presented for the use in the form of veterinary formulations, which may be prepared by methods that are conventional in the art.

The following examples are intended to illustrate, but not limit, the invention.

Materials and Methods

Synthesis of Nucleoside Compounds

Synthesis of the above noted 5-substituted pyrimidine derivatives can be accomplished by methods known in the art, for example as described in Applicant's patent literature, PCT/US98/16607 and PCT/US99/01332.

One method requires treatment of 5-chloromercuri-2'-deoxyuridine with haloalkyl compounds, haloacetates or haloalkenes in the presence of $Li_2PdCl_4$ to form, through an organopalladium intermediate, the 5-alkyl, 5-acetyl or 5-alkene derivative, respectively (Wataya, Y. et al. (1979) and Bergstrom, D. E. et al. (1984)). Another example of C5-modification of pyrimidine nucleosides and nucleotides is the formation of C5-trans-styryl derivatives by treatment of unprotected nucleotide with mercuric acetate followed by addition of styrene or ring-substituted styrenes in the presence of $Li_2PdCl_4$ (Bigge, et al. (1980)).

Pyrimidine deoxyribonucleoside triphosphates can be derivatized with mercury at the 5 position of the pyrimidine ring by treatment with mercuric acetate in acetate buffer at 50° for 3 hours (Dale, et al. (1973)). Such treatment also would be expected to be effective for modification of monophosphates. Alternatively, a modified triphosphate can be converted enzymatically to a modified monophosphate, for example, by controlled treatment with alkaline phosphatase followed by purification of monophosphate. Other moieties, organic or nonorganic, with molecular properties similar to mercury but with preferred pharmacological properties could be substituted. For general methods for synthesis of substituted pyrimidines see, for example, U.S. Pat. Nos. 4,247,544, 4,267,171, and 4,948,882 and Bergstrom, D. E. et al. (1981). The above methods would also be applicable to the synthesis of derivatives of 5-substituted pyrimidine nucleosides and nucleotides containing sugars other than ribose or 2'-deoxyribose, for example 2'-3'-dideoxyribose, arabinose, furanose, lyxose, pentose, hexose, heptose, and pyranose. An example of a 5-position substituent is the halovinyl group, e.g. (E)-5-(2-bromovinyl)-2'-deoxyuridylate (Barr, P. J. et al. (1983)).

Alternatively, 5-bromodeoxyuridine, 5-iododeoxyuridine, and their monophosphate derivatives are available commercially from Glen Research, Sterling, Va. (USA), Sigma-Aldrich Corporation, St. Louis, Mo. (USA), Moravek Biochemicals, Inc., Brea, Calif. (USA), ICN, Costa Mesa, Calif. (USA) and New England Nuclear, Boston, Mass. (USA). Commercially-available 5-bromodeoxyuridine and 5-iododeoxyuridine can be converted to their monophosphates either chemically or enzymatically, through the action of a kinase enzyme using commercial available reagents from Glen Research, Sterling, Va. (USA) and ICN, Costa Mesa, Calif. (USA). These halogen derivatives could be combined with other substituents to create novel and more potent antimetabolites.

In one aspect, the structures at the 5-position of the 1,5-substituted pyrimidine derivatives or analogs in Formulae A, B and C are referred to as the tethers because they connect a proposed leaving group (toxophore) to the heterocycle.

In one aspect, the tether also contains a spacer between the toxin and the pyrimidine ring can be unsaturated, e.g., vinyl, allyl, and propargyl units are simple, small, and readily accessible synthetically. The vinyl and allyl units have the advantage that they can be prepared in either of two non-interconvertible geometric isomeric forms. Alternatively, synthesis based on the structure of BVdU monophosphate and features a proposed leaving group/toxin directly attached to the terminus of a (poly)vinyl substituent at C5 of the pyrimidine ring. This is the vinyl tether approach. A yet further approach is based on the structure of TFPe-dUMP and is similar to the vinyl tether approach but has a methylene unit separating the proposed leaving group/toxin and the unsaturated unit and thus contains an allyl or propargyl unit. This is the allyl tether approach.

5-Alkylidenated 5,6-dihydrouracils similar in structure to the intermediate common to both the vinyl and allyl tether approach mechanisms have been synthesized recently (Anglada, J. M. et al. 1996). A C5 methylene intermediate produced by the enzyme thymidylate synthase TS was demonstrated by trapping studies (Barrett, J. E. et al. (1998)).

The compounds of Formula B are defined by the structure of the uracil base, or modified uracil base present. These classes are compounds where: 1) the base is a furanopyrimidinone derivative of uracil; 2) the base is 6-fluoro uracil; 3) the base is 4-hydrazone substituted uracil derivative; and 4) the base is uracil. In one aspect, the uracil or modified uracil derived base is used to synthesize compounds substituted with toxic leaving groups at the 5 position, attached by an electron conduit tether at this 5 position, and including an appropriate spacer moiety between the electron conduit and the toxic leaving group. The compounds can be unphosphorylated, 5' monophosphate, 5' phosphodiester, or 5' protected ("masked") deoxyuridines or comparable derivatives of alternative carbohydrate moieties, as described below. Protected 5-substituted deoxyuridine monophosphate derivatives are those in which the phosphate moiety has been blocked through the attachment of suitable chemical protecting groups. In another embodiment, 5-substituted uracil or uridine derivatives are administered to cells containing nucleoside kinase activity, wherein the 5-substituted uracil/uridine derivative is converted to a 5-substituted uridine monophosphate derivative. Uridine derivatives may also be modified to increase their solubility, cell penetration, and/or ability to cross the blood-brain barrier.

Synthesis of Compounds with Propargyl Tethers

The synthesis of propargylic and allylic alcohol-equipped 2'-deoxyuridines are reported in the literature. For example, Barr, P. J. and Robins, M. J. (1981) and Balzarini, J. et al. (1985).

Both 5-mercuri- (Ruth, J. L. et al. (1978)) and 5-iodouridines (Robins, M. J. et al. (1981)) readily condense with alkenes and alkynes in the presence of a palladium catalyst to afford C5 tether-equipped uridines. The latter route is the more often employed (Robins, M. J. et al. (1982) and Asakura, J. et al. (1988) and (1990)). High-yielding condensations of protected 5-iodo-2'-deoxyuridines with t-butyidimethylsilyl propargyl ether (Graham, D. et al. (1998); De Clercq, E. et al. (1983), methyl propargyl ether (Tolstikov, V. V. et al. (1997)) and even propargyl alcohol itself (Chaudhuri, N. C. et al. (1995) and Goodwin, J. T. et al. (1993)) have been achieved. The 3-hydroxy-1-propynyl substituent introduced by the latter reaction can also be accessed by DIBAL-H reduction of a methacrylate group (Cho, Y. M. et al. (1994)), itself arising from the same Heck reaction used in the synthesis of BVdU. These palladium-catalyzed reactions can be used to condense very long and elaborately-functionalized propargyl-based tethers to 5-iodo-2'-deoxyuridines. (Livak, K. J. et al. (1992) and Hobbs, F. W. Jr. (1989)). (Z)-Allyl-based tethers are generated by the partial hydrogenation of a propargylic precursor over Undiar catalyst (Robins, M. J. et al. (1983)) whereas the (E)-allyl-based ones are best prepared by Heck coupling of an (E)-tributyl-stannylated ethylene (Crisp, G. T. (1989)).

Closely following the literature procedures, a t-butyldimethylsilyl propargyl ether-equipped 3', 5'-di-O-protected 2'-deoxyuridine (Graham, D. et al. (1998), and De Clercq, E. et al. (1983)) can be prepared and a portion of it, converted to the corresponding (Z)-allyl ether, (Robins, M. J. et al. (1983)) is reduced. Because the TBAF-mediated removal of a TBDMS group generates an oxyanion that can be functionalized in situ, these TBDMS-protected propargyl- and (Z)-allytic-tethered nucleosides can serve as convenient precursors to some of the toxophore-equipped targets. For the (E)-allyl alcohol equipped nucleoside, the known O-tetrahydropyranyl ether derivative is prepared by the literature Heck coupling of an (E)-tributylstannylated ethylene (Crisp, G. T. (1989)).

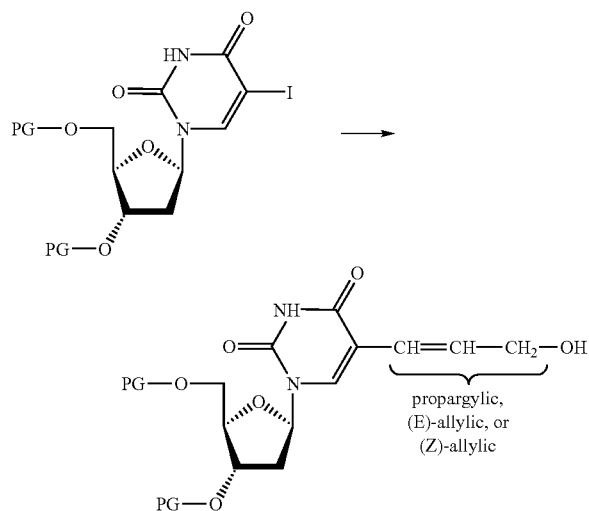

Using a two step literature protocol (Phelps, M. E. et al. (1980) and Hsiao, L. Y. et al. (1981)), the propargylic and (E) and (Z)-allylic alcohols are converted to their corresponding bis-aziridinyl phosphoramidates or thiophosphoramidates.

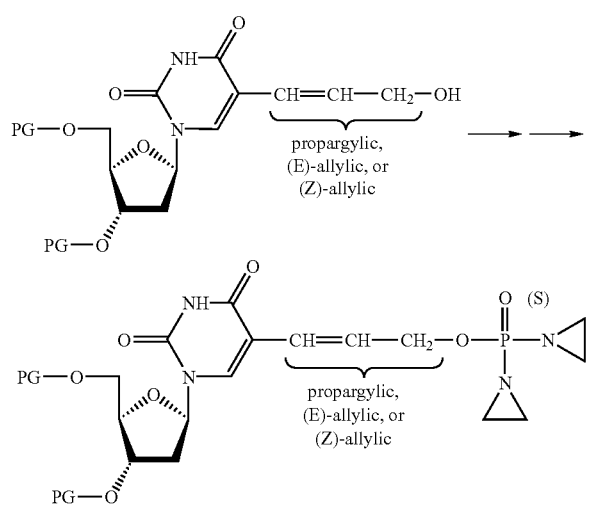

Synthesis of Furano-Pyrimidinones

Synthesis of furano-pyrimidinones begins with synthesis of a C5 propargylic—alcohol-equipped 2'-deoxyuridine. Furano-pyrimidinone compounds are then be formed from the O-tetrahydropyranyl ether derivative described above. Synthesis proceeds by reaction of the second carbon of the propargyl bond with the oxygen attached to the C4 position of the pyrimidine ring to yield a fluorescent furano-pyrimidinone which can be readily separated from the reaction mix. Such compounds provide an additional basis for synthesis of compounds through various combinations of specific electron conduits, spacers and toxic leaving groups.

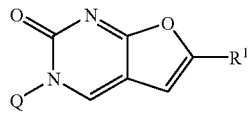

Furo[2,3-d]pyrimidinone nucleosides (represented by the above generic structure) were prepared by condensing 2',3'-di-O-p-toluoyl or 2',3'-di-O-acetyl-5-iodo-2'-deoxyuridine with 1-(tetrahydropyranyloxy)-2-propyne (Jones, R. G. and Mann, M. J. (1953)) under conditions known to promote the formation of these fluorescent compounds (Robins, M. J. et al.(1983)). Base-catalyzed removal of the carbohydrate protecting groups gave the 6-(tetrahydropyran-2-yloxymethyl)-substituted bicyclic nucleoside which was either subjected to standard acidic THP group hydrolysis (TFA in $CH_2Cl_2$) or was regioselectively 5'-phosphoramidated by the same procedure used to prepare BVdU-PA and 5FUdR-PA. After the phosphoramidation, the THP group can be removed by acidic hydrolysis.

Compounds Based on Furano-Pyrimidinones

Examples of synthesis of compounds having a structure of the class shown are as follows.

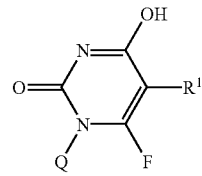

Proposed toxic $R^4$ leaving groups can be attached to the furan-2 methyl alcohol using methods similar to those employed to attach toxic leaving groups to the hydroxyl on the C5 propargyl uridine compound, as explained above. A variety of alternative toxic leaving groups are envisioned. In addition, modifications to the length and composition of the $R^2$ electron conduit component and of the composition of the $R^3$ spacer element are also envisioned.

Compounds based on furano-pyrimidinones can also consist of variously modified "Q" moieties. Compounds can have a free 5' hydroxyl, a 5' monophosphate, or a 5' phosphoramidate group attached to alternative carbohydrate groups. A method for synthesis of such phosphoramidate compounds is accomplished by reacting a 2-deoxy 3'-hydroxy, 5'-hydroxy unprotected nucleotide with a phosphochloridate in the presence of an HCl scavenger. In one aspect, the phosphochloridate comprises a phosphorus substituent which is derived from an amino acid such as alanine. For example, the phosphochloridate can be phenyl-L-methoxyalanine phosphorochloridate.

C6 Fluoro Uridine and C4 Hydrazone Based Compounds

The introduction of fluorine at the C6 position can be synthesized by following the synthetic descriptions of Krajewskas and Shugar (1982), who describe the synthesis of a number of 6 substituted uracil and uridine analogs.

Chemistry facilitating substitutions at the C4 position of the pyrimidine base are known by those skilled in the art. Examples of literature descriptions include Wallis et al. (1999); Negishi, et al. (1996), Barbato et al. (1991), Barbato, et al. (1989) and Holy et al. (1999). These synthetic techniques also enable combinations of substitutions, for instance at the C4 and C5 positions of the pyrimidine ring (Pluta, et al. 1999) or the C2 and C4 positions of the pyrimidine ring (Zeid, et al. (1999)).

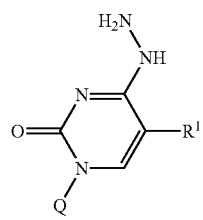

In another embodiment of the invention, compounds are synthesized by addition of alternative electron conduits, spacer moieties and toxic leaving groups to either the C6 fluoro-uridine base or the C4 hydrazone modified pyrimidine. Methods described above for synthesis of 2-deoxyuridine based compounds can again be employed for the synthesis of such molecules.

Synthesis of Nucleoside Phenyl Methoxyalaninyl Phosphoramidates

The use of phosphoramidates as phosphate prodrugs for nucleotides was reported by McGuigan, C. et al. (1993) and McGuigan, C. et al. (1994). The phospharamidates were synthesized by reacting 2',3'-dideoxynucleosides with phenyl methoxyalaninyl phosphorochloridate (PMPC).

Since only one hydroxyl group is present, these reactions usually proceed smoothly. In compounds where more than one hydroxyl group is present, the appropriately protected nucleoside may be required. Since the 5'-OH group of 2'-deoxynucleosides is much less hindered than the 3'-OH group, selective phosphoramidation with PMPC is possible under carefully controlled conditions. Both BVdU and 5FUdR condensed with PMPC in the presence of N-methylimidazole in anhydrous $CH_2Cl_2$ to give the corresponding phosphoramidates. In both cases, the desired product was readily separable from the starting material using column chromatography on silica gel. The synthetic scheme is summarized below.

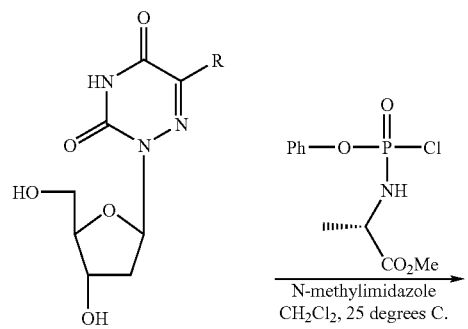

-continued

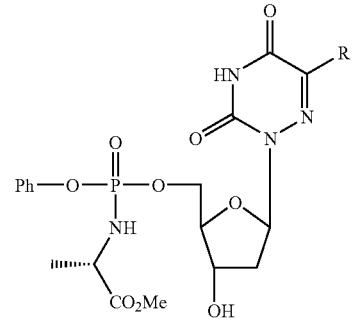

The following synthetic examples are intended to illustrated, but not limit the invention.

EXAMPLES 1 and 2

Synthesis of Compounds with Propargyl Tethers

Using the general synthetic procedure described supra, bis-aziridin-1-yl-phosphinic acid 3-[2-deoxyuridin-5-yl]-prop-2-ynyl ester was synthesized and analyzed by $^1$H NMR to yield the following result: $^1$H NMR (($CD_3$)$_2$SO). Salient features: δ 8.28 (d, 1, H6), 6.10 (pseudo-t, 1, H1'), 5.26 (m, exchanges with $D_2O$, 1, 3'-OH), 5.13 (m, exchanges with $D_2O$, 1, 5'-OH), 4.81 (q or dd, 2, propargyl-$CH_2$), 4.24 (m, 1, H3'), 3.57 (m, 2, 5'-$CH_2$), 2.15–2.0 (m, 8, aziridine-$CH_2$).

Bis-aziridin-1-yl-phosphinothioic acid 3-[2-deoxyuridin-5-yl]-prop-2-ynyl ester was also synthesized and analyzed by $^1$H NMR to yield the following result: $^1$H NMR (($CD_3$)$_2$SO). Salient features: δ 8.29 (d, 1, H6), 6.10 (pseudo-t, 1, H1'), 5.22 (m, exchanges with $D_2O$, 1, 3'-OH), 5.10 (m, exchanges with $D_2O$, 1, 5'-OH), 4.88 (q or dd, 2, propargyl-$CH_2$), 4.31 (m, 1, H3'), 3.52 (m, 2, 5'-$CH_2$), 2.15–2.0 (m, 8, aziridine-$CH_2$).

EXAMPLES 3 to 8

Synthesis of Furano-Pyrimidinones

Using the general synthetic procedure described supra, the following compounds were prepared.

EXAMPLE 3

3-(2-Deoxy-β-D-ribofuranosyl)-6-(tetrahydropyran-2-yloxymethyl)furo[2,3-d]pyrimidin-2(3H)-one. $^1$H NMR (($CD_3$)$_2$SO) δ 8.80 (s, 1, H4), 6.74 (s, 1, H5), 6.16 (pseudo-t, 1, H1'), 5.27 (d, exchanges with $D_2O$, 1, 3'-OH), 5.12 (t, exchanges with $D_2O$, 1, 5'-OH), 4.72 (m, 1, THP-H2), 4.56 (q, 2, $CH_2$OTHP), 3.92 (m, 1, H4'), 3.64 (m, 2, 5'-$CH_2$), 2.40 (m, 1, H2'a), 2.03 (m, 1, H2'b), 1.68 and 1.50 (m, 8, THP). Low-resolution mass spectrum (DCI-$NH_3$) on bis-TMS derivative, m/z 323 (B+TMS+H$^+$), 511 (MH$^+$), 583 (M+TMS$^+$).

EXAMPLE 4

3-(2-Deoxy-β-D-ribofuranosyl)-6-(hydroxymethyl)furo[2,3-d]pyrimidin-2(3H)-one. $^1$H NMR (($CD_3$)$_2$SO) δ 12.0 (bs, 1, OH), 8.24 (s, 1, H4), 6.53 (s, 1, H5), 5.51 (pseudo-t, 1, H1'), 4.42 (m, 2, $CH_1$OH). Low-resolution mass spectrum (DCI-$NH_3$), m/z 167 (B+2H$^+$), 184 (B+$NH_4^+$).

EXAMPLE 5

1-[6-(Tetrahydropyran-2-yloxymethyl)furo[2,3-d]pyrimidin-2(3H)-on-3-yl]-2-deoxy-β-D-ribofuranos-5-yl phenyl methoxy-L-alaninylphosphoramidate. $^1$HNMR ((CD3)2SO) complicated due to presence of diastereomers. Salient features: δ 8.62 and 8.59 (each s, each 1, H4), 7.4–7.1 (m, 5, PhO), 6.61 and 6.60 (each s, each 1, H5), 6.25 (m, 1, H1'), 4.56 (q, 2, propargyl-CH$_2$), 3.56 and 3.54 (each s, each 3, CO$_2$Me), 2.0 (m, 1,H2'b), 1.22 (m, 3, alaninyl-α-Me). Low-resolution mass spectrum (DCI-NH3), m/z 167 (B+2H$^+$), 184 (B+H$^+$+NH$_4^+$−THP).

EXAMPLE 6

1-[6-(Hydroxymethyl)furo[2,3-d]pyrimidin-2(3H)-on-3-yl]-2-deoxy-β-D-ribofuranos-5-yl phenyl methoxy-L-alaninylphosphoramidate. $^1$H NMR (CDCl$_3$) complicated due to presence of diastereomers. Salient features: δ 8.5 (s, 1, H4), 7.4–7.1 (m, 5, PhO), 6.36 and 6.30 (each s, each 1, H5), 6.23 (m, 1, H1'), 3.67 and 3.65 (each s, each 3, CO$_2$Me), 2.69 (m, 1, H2'a), 2.10 (m, 1, H2'b), 1.35 (m, 3, alaninyl-α-Me). Low-resolution mass spectrum (DCI-NH$_3$), m/z 525 (MH$^+$), 595 (MNH$_4^+$).

EXAMPLE 7

The 4-nitrophenyl ether derivative of 5-(3-hydroxy-1-propynyl)-2'-deoxyuridine was prepared according to standard ether synthesis as shown below.

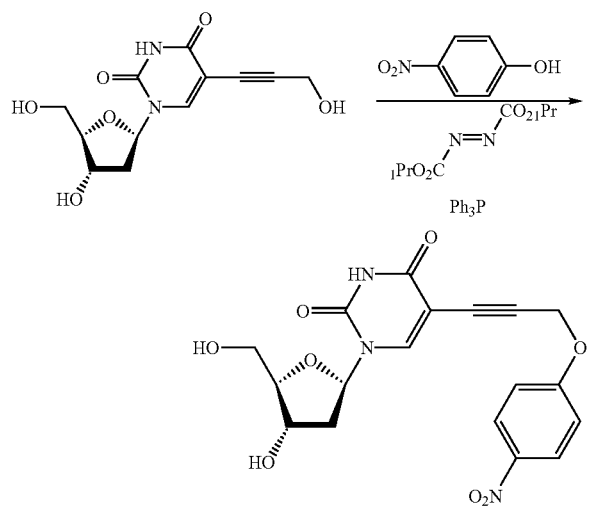

EXAMPLE 8

5-[3-(4-Nitrophenoxy)-1-propynyl]-2'-deoxyuridine

A solution of pre-dried 5-(3-hydroxy-1-propynyl)-2'-deoxyuridine (Robins, M. J. et al. (1983)) (565 mg, 2 mmol) in 40 mL of anhydrous THF under argon was treated with 4-nitrophenol (696 mg, 5 mmol), triphenylphosphine (787 mg, 3 mmol), and diisopropyl azodicarboxylate (590 liters, 3 mmol), and the reaction mixture heated at 60° C. until the solution was clear, and then 1 hour longer. The mixture was allowed to cool to 23° C. and then it was evaporated onto SiO$_2$ and purified by chromatography using MeOH/CH$_2$Cl$_2$ as eluent to afford 107 mg (13%) of the desired ether product: melting point 112–118° C. $^1$H NMR ((CD$_3$)$_2$SO) δ 11.65 (s, exchanges with D$_2$O, 1, NH), 8.29 (s, 1, H6), 8.24 (d, J=9.3 Hz, 2, m-ArH), 7.23 (d, J=9.3 Hz, 2, o-ArH), 6.09 (pseudo-t, 1, H1'), 5.17 (s, 2, propargyl-CH$_2$), 4.22 (m, 1, H3'), 3.80 (m, 1, H4'), 3.59 (m, 2, 5'-CH$_2$), 2.13 (pseudo-t, 2, 2'-CH$_2$). Low-resolution mass spectrum (DCI-NH$_3$) on per-trimethylsilyated material, m/z 547 [M(TMS)$_2$H$^+$], 565 [M(TMS)$_2$NH$_4^+$], 620 [M(TMS)$_3$H$^+$].

EXAMPLE 9

5-(4-Carbethoxy-1,3-butadienyl)-2'-dexoyuridine (a) 5-(Carbomethoxyvinyl)-2'-deoxyuridine-3',5'-bis(tetrahydro-2H-pyran-2-yl)ether (I)

A slurry of 5-(carbomethoxyvinyl)-2'-deoxyuridine (3.0 g, 9.6 mmol), 3,4-dihydro-2H-pyran (22 mL, 21.3 mmol) and pyridinium p-toluenesulfonate (PPTS, 0.242 g, 0.96 mmol) in dimethylformamide (DMF, 5 mL) was stirred at 50° C. for 18 hours. The resulting solution was concentrated in vacuo (bath temperature 45° C.) to give a thick, pale yellow oil. The oil was dissolved in EtOAc and the solid was filtered. The solution was again concentrated. The oil obtained was purified by column chromatography on silica gel using 50–75% EtOAc/hexane as eluent to give 3.81 g (85%) of pure product as a colorless oil.

(b) 5-(3-Hydroxyprop-1-enyl)-2'-deoxyuridine-3',5'-bis(tetrahydro-2H-pyran-2-yl)ether (II)

A solution of (I) (3.5 g, 7.27 mmol) in CH$_2$Cl$_2$ (14 mL) was cooled to −78° C. in a dry ice/acetone bath. Diisobutylaluminum hydride (DIBAL-H) in toluene (1.0 M, 24 mL, 24.0 mmol) was added dropwise over 2 hours while the temperature was maintained at −78° C. The solution was stirred at −78° C. for an additional 2 hours and MeOH (2.5 mL) was added dropwise to destroy any excess DIBAL-H. The reaction mixture was cannulated into a mixture of 30% citric acid solution (50 mL), ice (25 g) and EtOAc (30 mL) over ca. 20 minutes. The phases were separated and the aqueous phase was extracted with EtOAc (2×25 mL). The combined organic phase was washed with saturated NaHCO$_3$ (20 mL) and brine (20 mL), dried over MgSO$_4$ and concentrated to give 3.288 g (100%) of colorless oil.

(c) 5-(3-Oxoprop-1-enyl)-2'-dexoyuridine-3',5'-bis(tetrahydro-2H-pyran-2-yl)ether (III)

To a solution of crude (II) obtained from above (1.988 g, 4.4 mmol) in CH$_2$Cl$_2$ (9 mL) was added solid pyridinium dichromate (PDC; 1.82 g, 4.8 mmol) with water cooling. The suspension was stirred while acetic acid (0.4 mL) was added dropwise. The water bath was removed and the reaction was stirred at room temperature for 1 hour. The crude product was filtered through a pad of florisil (2×2.5 cm) and the florisil washed with 35 mL EtOAc. The brown solution obtained was filtered through another column of florisil (3.5 cm diam×2.5 cm height). The filtrate was concentrated to give 1.273 g (64% yield) of very light brown oil.

(d) 5-(4-Carbethoxy-1,3-butadienyl)-2'-dexoyuridine-3',5'-bis(tetrahydro-2H-pyran-2-yl)ether (IV)

(Carbethoxymethylene)triphenylphosphorane (0.32 mg, 0.92 mmol) was added to a solution of the crude aldehyde (III) (0.344 g, 0.77 mmol). The solution darkened and turned rust color. After 1 hour, (III) was completely consumed as judged by thin layer chromatography. The solvent was evaporated and the crude product was purified by column chromatography on silica gel using 35–45% EtOAc/hexane as eluent. The pure product (0.310 g, 78% yield) was obtained as colorless oil.

(e) 5-(4-Carbethoxy-1,3-butadienyl)-2'-dexoyuridine (V)

5-(4-Carbethoxy-1,3-butadienyl)-2'-dexoyuridine-3',5'-bis(tetrahydro-2H-pyran-2-yl)ether (IV) (0.637 g, 1.22 mmol) was dissolved in MeOH (1.5 mL) and PPTS (0.049 g, 0.16 mmol) was added. The solution was stirred at 50° C. for 7.5 hours and left at room temperature overnight. A white precipitate was formed. The reaction mixture was cooled to 0° C. and filtered to give pure (V) as a white solid (0.188 g). The filtrate was concentrated and chromatographed on silica gel using 50–100% EtOAc/hexane as eluent to give a further 0.180 g product. The total yield of the product was 0.368 g (86%).

$^1$H NMR (DMSO-$d_6$): 1.22 (3H, t, J=7 Hz), 2.17 (2H, br t, J=5.5 Hz), 3.55–3.75 (2H, m), 3.81 (1H, m), 4.12 (2H, q, J=7 Hz), 4.25–4.28 (1H, m), 5.19 (1H, t, J=4.8 Hz), 5.27 (1H, d, J=4.1 Hz), 5.98 (1H, d, J=14.5 Hz), 6.14 (1H, t, J=6.3 Hz), 6.75 (1H, d, J=14.5 Hz), 7.18–7.30 (2H, m), 8.30 (1H, s), 11.56 (1H, s).

EXAMPLE 10

5-(4-Carbomethoxy-1,3-butadienyl)-2'-dexoyuridine (Va)

A solution of triethylamine (3.9 mL, 28.2 mmol) in dioxane (12 mL) was deareated by bubbling nitrogen through for 15 minutes. Palladium acetate (0.60 g, 0.26 mmol) and triphenylphosphine (0.183 g, 0.70 mmol) were added and the solution was heated at 70° C. for 20 minutes to give a dark brown solution. 5-Iodo-3'-deoxyuridine (5.0 g, 14.1 mmol) and methyl 2,4-pentadienoate (2.5 g, 22.3 mmol) were added and the mixture was heated under reflux for 15 hours. The solvent and volatile components were evaporated in vacuo and the residue was partitioned between water (15 mL) and EtOAc (15 mL). The phases were separated and the aqueous phase was extracted twice with EtOAc (10 mL each). The combined organic phase was washed with brine and concentrated. The residue was dissolved in MeOH (15 mL) and allowed to cool to room temperature. The solid formed was collected by filtration, washed with a small quantity of MeOH and dried in vacuo to give 0.38 g brown powder.

$^1$H NMR (DMSO-$d_6$): 2.17 (2H, t, J=6.4 Hz), 3.55–3.70 (2H, m), 3.66 (3H, s), 3.82 (1H, q, J=3.6 Hz), 4.27 (1H, m), 5.18 (1H, t, J=4.9 Hz), 5.26 (1H, d, J=4.5 Hz), 5.99 (1H, d, J=14.4 Hz), 6.14 (1H, d, J=6.4 Hz), 6.74 (1H, d, J=14.8 Hz), 7.20–7.35 (2H, m), 8.30 (1H, s), 11.56 (1H, s).

The filtrate from above was concentrated and chromatographed on silica gel using 60–100% EtOAc/hexanes as eluent to give another 0.70 g of product as a brown foam. The combined yield was 1.08 g (22.6%).

EXAMPLE 11

5-(4-Carboxy-1,3-butadienyl)-2'-dexoyuridine (VI)

Method I 5-(4-Carbethoxy-1,3-butadienyl)-2'-dexoyuridine (V, from Example 9) (0.449 g, 1.28 mmol) was dissolved in 2N NaOH (3 mL) and stirred at 25° C. After 20 minutes, a precipitate was formed and TLC showed that the starting material was completely consumed. The mixture was cooled to 0° C. and acidified to pH 1 with 2N HCl. The resulting off-white solid was filtered off, washed with water and dried in vacuo to give 0.225 g (54%) product.

$^1$H NMR (DMSO-$d_6$): 2.12–2.19 (2H, m), 3.50–3.70 (2H, m), 3.75–3.85 (1H, m 4.24–4.29 (1H, m), 5.19 (1H, t, J=4.8 Hz), 5.27 (1H, d, J=4.2 Hz), 5.80–5.95 (1H, m), 6.14 (1H, t, J=6.4 Hz), 6.60–6.75 (1H, m), 7.15–7.25 (2H, m), 8.26 (1H, s), 11.56 (1H, s), 12.16 (1H, br s).

The filtrate and washings were combined and evaporated to dryness. The resulting sticky yellow solid was dissolved in MeOH from which a white precipitate was formed. The solid was filtered off to give an additional 0.200 g of product.

Method II

The title compound can also be prepared from 5-(4-carbomethoxy-1,3-butadienyl)-2'-dexoyuridine (Va, from Example 10) in comparable yield as mentioned above.

EXAMPLE 12

5-(4-Bromo-1E,3E-butadienyl)-2'-dexoyuridine (VIIa) and 5-(4-Bromo-1E,3Z-butadienyl)-2'-dexoyuridine (VIIb)

To a solution of 5-(4-carboxy-1,3-butadienyl)-2'-dexoyuridine (VI) (0.200 g, 0.62 mmol) in DMF (1 mL) was added KHCO$_3$ (0.185 g, 1.84 mmol) and the mixture was stirred for 20 minutes at 25° C. A solution of N-bromosuccinimide (0.117 g, 0.65 mmol) in DMF (0.3 mL) was added dropwise. Smooth gas evolution (CO$_2$) occurred throughout the addition. The resulting brown suspension was stirred for 2 hours at 25° C. at which time TLC showed that (VI) was completely consumed. Water (10 mL) was added to the suspension and the resulting solution was extracted with EtOAc (2×15 mL). The extract was dried over MgSO$_4$ and the solvent was evaporated in vacuo to give a yellow solid (178 mg, 80% yield) consisting of a mixture of two isomers as shown by $^1$H NMR. The crude product was separated by semi-preparative HPLC (reversed phase C18 column) using 20% acetonitrile in water as the mobile phase to give the following isomers:

5-(4-Bromo-1E,3Z-butadienyl)-2'-dexoyuridine: retention time 10.5 minutes; $^1$H NMR: (DMSO-d6): 2.11–2.18 (2H, m), 3.50–3.70 (2H, m), 3.80 (1H, distorted q, J=3.5 Hz), 4.25 (1H, br s), 5.08 (1H, br s), 5.25 (1H, br s), 6.15 (1H, t, J=6.5 Hz), 6.40 (1H, d, J=7 Hz), 6.53 (1H, d, J=15.6 Hz), 6.83 (1H, dd, J=7, 10 Hz), 7.39 (1H, dd, J=10, 15.6 Hz).

5-(4-Bromo-1E,3E-butadienyl)-2'-dexoyuridine: retention time 15.1 minutes; $^1$H NMR (DMSO-$d_6$): 2.12–2.16 (2H, m), 3.50–3.70 (2H, m), 3.80 (1H, q, J=3.2 Hz), 4.26 (1H, m), 5.13 (1H, br s), 5.25 (1H, br s), 6.14 (1H, t, J=6.5 Hz), 6.36 (1H, d, J=15.6 Hz), 6.67 (1H, d, J=13.1 Hz), 6.84 (1H, dd, J=11, 13.1 Hz), 7.04 (1H, dd, J=11, 15.6 Hz).

EXAMPLE 13

Using the procedures mentioned in Example 11, Method II, the following compounds can be obtained in a similar fashion: 5-(4-chloro-1,3-butadienyl)-2'-dexoyuridine (using N-chlorosuccinimide in place of N-bromosuccinimide in Step B); 5-(4-iodo-1,3-butadienyl)-2'-dexoyuridine (using iodine in sodium idodide in place of N-bromosuccinimide).

EXAMPLE 14

Phenyl N-methoxy-L-alaninyl Phosphorochloridate

L-alanine methyl ester hydrochloride (245.8 g; 1.76 mol) was placed in a 12 liter three-neck round bottom flask (equipped with a mechanical stirrer and thermometer) followed by 4.0 liters of dichloromethane. The mixture was stirred for 15 minutes at room temperature. Phenyl phosphodichloridate (370.0 g; 1.76 mol) was added to the mixture and stirring was continued for 15 minutes at room temperature. The flask was placed in the bath with dry ice and the stirring was continued for 20 minutes until a uniform suspension was formed.

Freshly distilled tri-n-butylamine (626.5 g; 3.38 mol) was added dropwise (~90 minutes) with vigorous stirring to the reaction mixture so that the temperature inside the flask was held at ~0° C. The bath was removed and the stirring was continued for 6 hours at room temperature. The solution was concentrated to ~2.84 liters by evaporating several portions of the mixture on a rotary evaporator and the mixture was sealed under argon and stored at −20° C. The product was 85% pure by phosphorus NMR to give an estimated concentration of phenylmethoxyalaninyl phosphochloridate of ~0.5 M.

EXAMPLE 15

5-(2-Bromovinyl)-2'-deoxyuridine phenyl N-methoxy-L-alaninyl phosphoramidate (NB1011)

The reaction was performed under argon atmosphere. 5-(2-bromovinyl)-2'-deoxyuridine (BVdU) (204 g; 612 mmol) was placed in three-neck 3 liter round bottom flask equipped with mechanical stirrer. The flask was placed in ice-water bath and 1600 mL (~800 mmol) of phenylmethoxyalaninyl phosphochloridate reagent were added using an addition funnel over 15 minutes with vigorous stirring of the reaction mixture, followed by the addition of 100 mL of N-methylimidazole over 5 minutes using syringe. After 5 minutes the mixture became clear and after 10 minutes the ice-water bath was removed to allow the mixture to warm up to room temperature while stirring was continued. The reaction was monitored by reversed phase HPLC and was complete in 3 hours. The reaction was quenched by the addition of 100 mL of methanol and the mixture was evaporated to an oil, re-dissolved in 6 liters of dichloromethane and passed through 800 g of silica gel. The major portion of BVdU-PA, referred to herein as NB1011, was passed through the column during the loading and finally the elution of NB1011 was completed by passing 5 liters of 5% methanol in dichloromethane. All fractions containing NB1011 were combined and evaporated to an oil, the residue was dissolved in 4 liters of ethyl acetate and the mixture was extracted with water (2×2 liters). The organic layer was dried with sodium sulfate, filtered, and washed with ethyl acetate (3×300 mL). The combined filtrate and washings were evaporated to produce a lightly colored white foam; total weight ~540 g.

The crude product was purified by two silica gel chromatography using 0–5% MeOH in $CH_2Cl_2$ and 10% MeOH in $CH_2Cl_2$, respectively, as eluent. The yield of product (>98% pure) was 64 g.

EXAMPLE 16

Using the methods described in Example 15, the phenyl N-methoxy-L-alanyl phosphoramidates of the following nucleosides were prepared:

5-(4,4-dibromo-1,3-butadienyl)-2'-deoxyuridine;
5-(2-chlorovinyl)-2'-deoxyuridine;
5-trifluoromethyl-2'-deoxyuridine;
5-(4-carbethoxy-1,3-butadienyl)-2'-deoxyuridine;
5-(4-carbomethoxy-1,3-butadienyl)-2'-dexoyuridine;
5-(4-bromo-1E,3E-butadienyl)-2'-deoxyuridine;
5-(4-bromo-1E,3Z-butadienyl)-2'-deoxyuridine;
5-(trimethylsilylethynyl)-2'-deoxyuridine;
5-(ethynyl)-2'-deoxyuridine;
5-(1-decynyl)-2'-deoxyuridine;
3-(2'-deoxy-β-D-ribofuranosyl)-2,3-dihydrofuro[2,3-d]pyrimidin-2-one; and
3-(2'-deoxy-β-D-ribofuranosyl)-6-octyl-2,3-dihydrofuro[2,3-d]pyrimidin-2-one.

Chemical assays for products, for example, where a reaction product is an anti-metabolite of the bromovinyl-derivatives of dUMP, are described in the Examples provided below or by Barr, P. J. et al. (1983).

EXAMPLE 17

Induction and Assessment of Arthritis

Arthritis was induced in male DBA/1 mice (8–10 weeks old) by intradermal injection of bovine type II collagen, purified in-house at the Kennedy Institute of Rheumatology as previously described (Miller, E. J. et al. (1972)). Collagen was administered in complete Freund's adjuvant (Difco, Detroit, Michigan). Onset of arthritis was variable, occurring from Day 14 up to Day 40 after immunization. Arthritis onset was considered to occur on the day that swelling and/or erythema were observed. Clinical score is a composite of disease severity and the number of limbs affected, and was monitored daily from onset of disease and used as an assessment of disease progress. The scoring used was: 0, Normal; 1, slight swelling with erythema; 2, pronounced swelling; 3, joint rigidity. In addition, the extent of paw swelling reflects the degree of edema in affected limbs. Arthritis increased progressively over 10 days as reflected by both clinical score and paw swelling.

EXAMPLE 18

Treatment of Animals with Anti-TNF or NB 1011

Anti-TNF antibody was used in these experiments was as described by Marinova-Mutafchieva, L. et al. (2000). NB1011 was administered daily by intraperitoneal administration at 2.5 mg total dose per day. Anti-TNF antibody was compared with NB1011 because, at present, antiTNF antibody is the optimal single agent for treatment of collagen induced arthritis (Marinova-Mutafchieva, L. et al. (2000)).

Success in this model has been shown to be predictive for clinical success in the development of new agents to treat inflammatory disease, especially rheumatoid arthritis (Elliott et al. (1994); Feldmann et al. (1998)). This model therefore represents an ideal setting for establishing proof of concept for new agents to treat rheumatoid arthritis, and potentially other autoimmune and inflammatory diseases.

Figure 2:
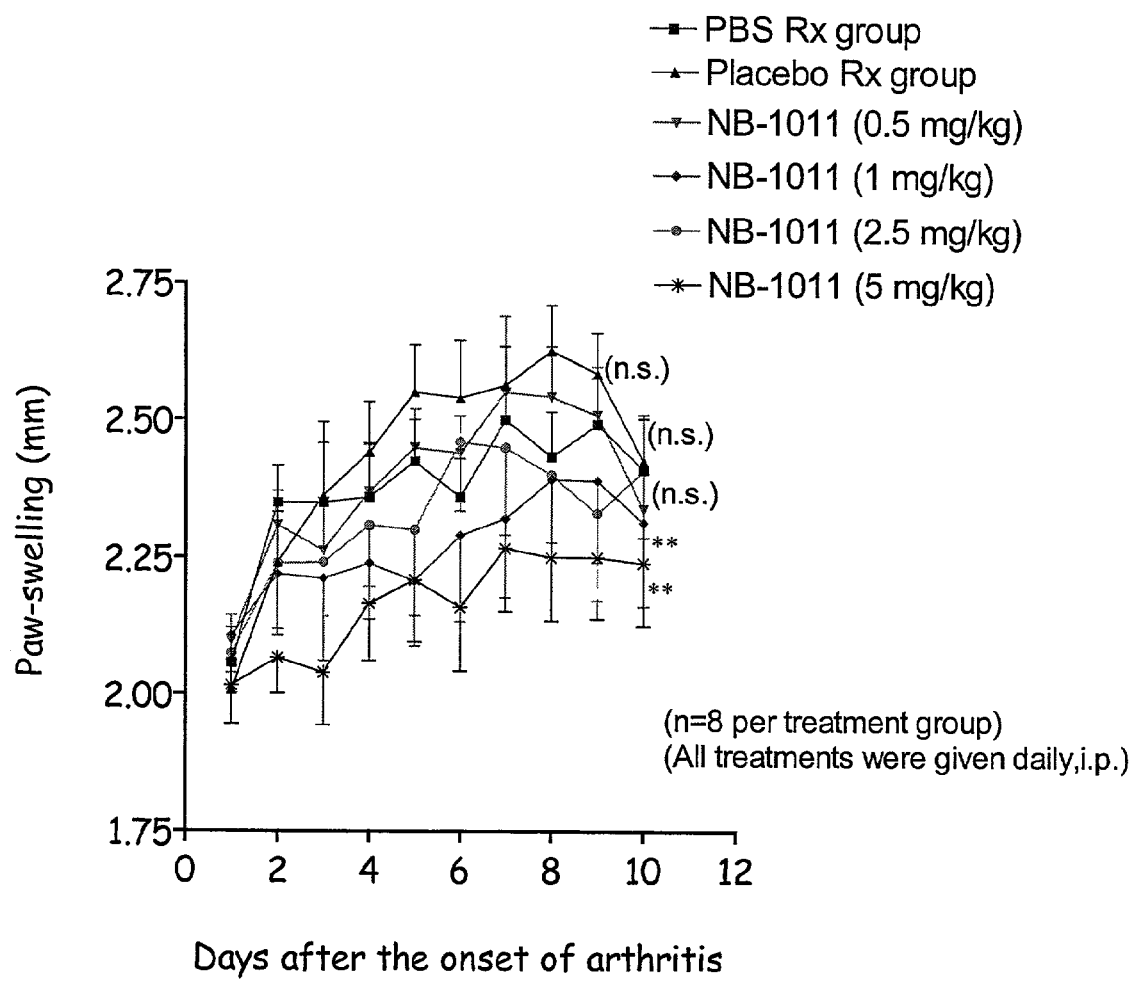
FIG. 2 shows therapeutic effect on paw swelling in animals with collagen-induced arthritis.
Figure 3:
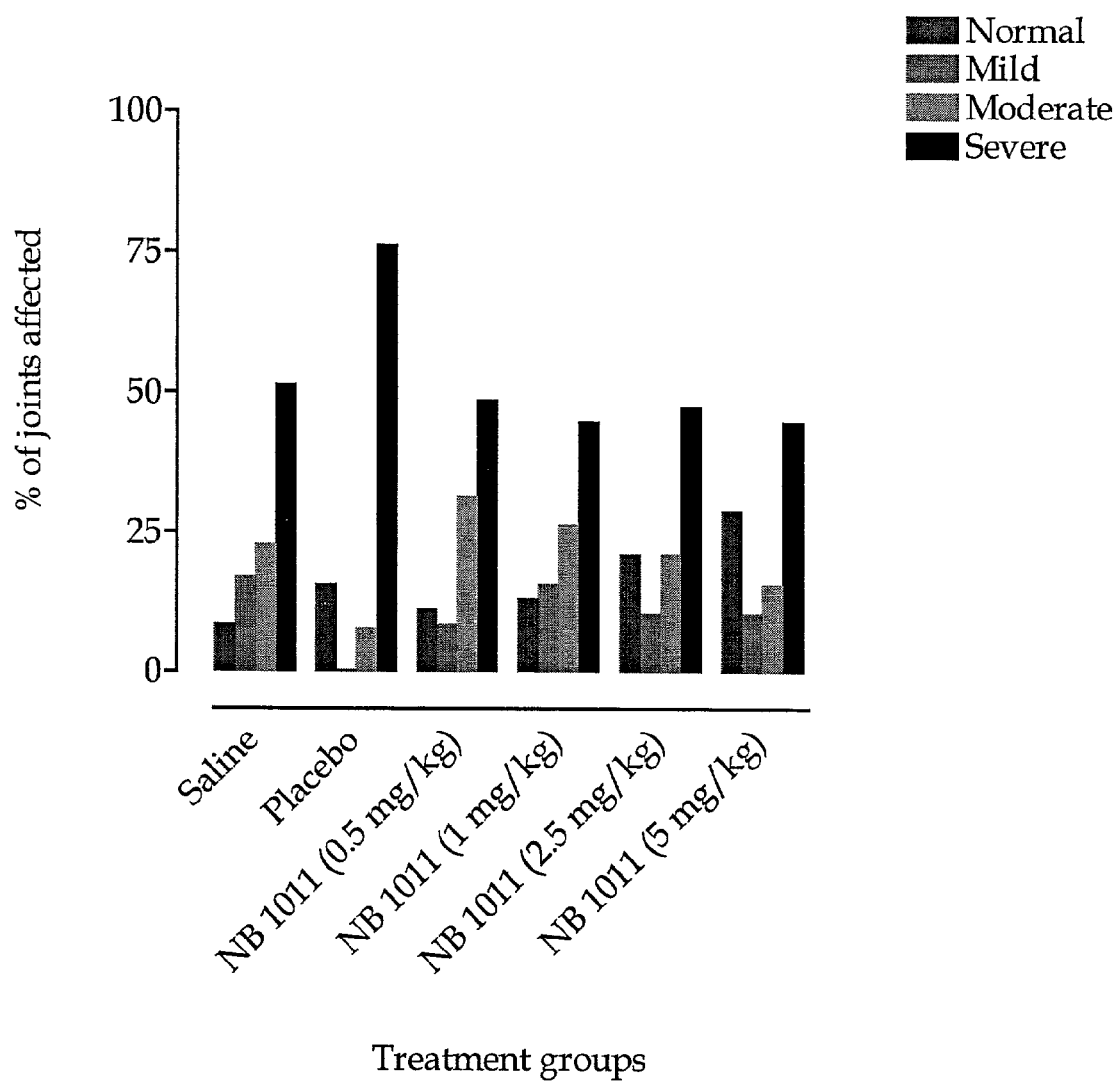
FIG. 3 shows histological evaluation of all joints performed by an observer blinded to the treatments received. This figure represents the percentage of joints exhibiting normal, mild or moderate to severe arthritic changes in the joint architecture in different treatment groups. Chi-square test (2×2 correlation) was done to calculate statistical significance of data. P<0.05 (*) was considered significant.

Following immunization with collagen, mice were maintained until a significant clinical score for disease progression was achieved (between 2.5 and 3.5, see FIG. 1 and Methods). Mice were then treated with control saline injections, NB1011, or with anti-TNF antibody as a positive control. The results (FIG. 1) show that the NB1011-treated group exhibited significant disease suppression (p<0.05), similar to the anti-TNF control, when compared with the saline-treated control group. There was no significant difference between the NB1011 and anti-TNF groups with regard to clinical score. Paw swelling is an alternative measure of CIA disease severity. When paw swelling was used as a criteria for disease suppression, comparable results were observed (FIG. 2). In this second measure of efficacy, both the NB1011 and anti-TNF groups demonstrated significant disease suppression as compared to the saline-treated control group (p<0.05). Again, there was no significant difference between the NB1011 and anti-TNF groups, although suppression of swelling may have been less dramatic with NB1011. A further significant outcome of this work is that by comparison with earlier reported work, NB1011 appears to have activity superior to anti-angiogenesis agents, an anti-CD4 immunosuppressive agent, and cannabidiol, a third experimental agent currently being considered for use to treat rheumatoid arthritis, and potentially other autoimmune and inflammatory disorders (Malfait, A. M. et al. (2000); Miotla, J. et al. (2000); Marinova-Mutafchieva, L. et al. (2000)).

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

REFERENCES

Abraham et al. (1996) *J. Med. Chem.* 39:4569–4575
Akdas, A. et al. (1996) *Eur. Urol.* 29(4):483–486
Akoi, M. et al. (1999) *Hypertension* 34(2):192–200
Almasan, A. et al. (1995a) *Proc. Natl. Acad. Sci. USA* 92:5436–5440
Almasan, A. et al. (1995b) *Cancer Metastases Rev.* 14:59–73
Anglada, J. M. et al. (1996) *J. Heterocycl. Chem.* 33:1259–1270
Antelman, D. et al. (1995) *Oncogene* 10:697
Asakura, J. et al. (1988) *Tetrahedron Lett.* 29:2855–2858
Asakura, J. et al. (1990) *J. Org. Chem.* 55:4928–4933
Aschele, C. et al. (1999) *J. Chem. Oncol.* 17(6):1760–1770
Aupperle, K. R. et al. (1998) *Am. J. Pathol.* 152(4):1091–8
Balzarini, J. et al. (1985) *Methods Find. Exp. Clin. Pharmacol.* 7:19–28
Balzarini, J. et al. (1996) *Proc. Natl. Acad. Sci. USA* 93:7295–7299
Banerjee, D. et al. (1995) *Acta Biochem. Pol.* 42:457
Banerjee, D. et al. (1998) *Cancer Res.* 58:4292–4296
Barbato, et al. (1989) *Nucleosides Nucleotides* 8(4):515–528
Barbour, K. W. et al. (1992) *Molec. Pharmacol* 42:242–248
Barr, P. J. and Robins, M. J. (1981) *J. Med. Chem.* 24(12):1385–1388
Barr, P. J. et al. (1983) *Biochemistry* 22:1696–1703
Barreft, J. E. et al. (1998) *J. Am. Chem. Soc.* 120:449–450
Benzaria et al. (1996) *J. Med. Chem.* 39: 4958
Bergstrom, D. E. et al. (1981) *J. Org. Chem.* 46(7):1432–1441
Bergstrom, D. E. et al. (1984) *J. Med. Chem.* 27:279–284
Bertino, J. R. et al. (1996) *Stem Cells* 14:5
Bigge, et al (1980) *J. Amer. Chem. Soc.* 102:2033–2038
Callahan, A. P. et al. (1989) Comm. Nucl. Med. 20:3–6
Carreras, C. W. and Santi, D. V. (1995) *Annu. Rev. Biochem.* 64:721–762
Carson, D. A. and Haneji, N. (1992) Nature Medicine 5(7):731–732
Carter, P. et al. (1992) *Proc. Natl. Acad. Sci. USA* 89:4285–4289
Chadhuri, N. C. et al. (1995) *J. Am. Chem. Soc.* 117: 10434–10442
Chen, L. et al. (1996) *Cancer Res.* 56:1331–1340
Cho, Y. M. et al. (1994) *Tetrahedron Lett.* 25:1149–1152
Clarke, R. (1996) *Breast Cancer Res. Treat.* 39:1–6
Clayman, G. L. (2000) *Semin Oncol* 27(4 Suppl 8):39–43
Cobleigh, M. A. et al. (1999) *J. Clin. Oncol.* 17(9):2639–2648
Connors, T. A. and Knox, R. J. (1995) *Stem Cells* 13:501–511
Copur, S. et al. (1995) *Biochem. Pharm.* 49(10):1419–1426
Cordon-Cardo, C. and Prives, C. (1999) *J. Exp. Med.* 190(10):1367–1370
Crisp, G. T. (1989) *Synth. Commun.* 19:2117–2123
Cruickshank, K. A. et al. (1988) *Tetrahedron Lett.* 29:5221–5224
Dale, et al. (1973) *Proc. Natl. Acad. Sci. USA* 70:2238–2242
DeClercq, E. et al. (1978) *Proc. Intl. Chemo.* 1(1):352–354
DeClercq, E. et al. (1983) *J. Med. Chem.* 26:661–666
DeClercq, E. et al. (1994) *Nucl. And Nucleotides* 13(687): 1271–1295
DeClercq, E. et al. (1997) *Clin. Micro. Review* 10(4): 674–693
DiCiommo et al. (2000) *Cancer Biology* 10:225–269
Dicken, A. P. et al. (1993) *Proc. Natl. Acad. Sci. USA* 90:11797–11801
Dirven, H. A. et al. (1995) *Cancer Res.* 55:1701–1706
Dorr, R. T. and Von Hoff, D. D., eds. (1994) "Cancer Chemotherapy Handbook" 2nd ed. (Appleton and Lange), pp. 768–773
Dunn, W. J. et al. (1996) *J. Med. Chem.* 39:4825–4832
Dyer, R. L. et al. (1991) *Nucl. Acids Chem.* 4:79–83
Edler, D. et al. (2000) *Clin. Cancer Res.* 6(2):488–492
Elliott et al. (1994) *Lancet* 344(8930): 1105–1110
Fan, J. and Bertino, J. (1987) *Oncogene* 14:1191–1200
Farquhar, J. et al. (1994) *J. Med. Chem.* 37:3902–3909
Farquhar, J. et al. (1995) *J. Med. Chem.* 38:488–495
Feldmann et al. (1998) *Springer Semin. Immunopath.* 20(1–2):211–228
Freed, et al. (1989) *Biochem. Pharmacol.* 38:3193–3198
Freemantle, S. J. et al. (1995) *Br. J. Cancer* 71:925–930
Fries, K. M. et al. (1995) *J. Med. Chem.* 38:2672–2680
Funk, J. O. (1999) *Anticancer Res.* 19(6A):4772–4780
Goodwin, J. T. et al. (1993) *Tetrahedron Lett.* 34:5549–5552
Gorlick, R. and Bertino, J. R. (1999) *Semin Oncol* 26(6): 606–11
Gottesman, M. M. et al. (1995) *Annu. Rev. Genet.* 29:607
Graham, D. et al. (1998)*J. Chem. Soc. Perkin Trans.* 1:1131–1138
Guevara, N. V. et al. (1999) *Nat Med* 5(3):335–9
Han et al. (1999) *Arthritis Rheum* 42(6): 1088–92
Haskell, C. M. ed., (1995) *Cancer Treatment* 4th Ed., W.B. Saunders Co., Philadelphia, Pa.
Hayashi, K. (2000) *Rheumatology (Oxford)* 39(3):262–6
Hobbs, F. W. Jr. (1989) *J. Org. Chem.* 54:3420–3422

Holy, et al. (1999) *J. Med. Chem.* 42(12):2064–2086
Hong, T. M. et al. (2000) *Am. J. Respir. Cell. Mol. Biol* 23(3):355–63
Hostetler, et al. (1997) *Biochem. Pharmacol.* 53:1815
Houze, T. A. (1997) *Tumour Biol.* 18:53–68
Hsiao, L. Y. et al. (1981) *J. Med. Chem.* 24:887–889
Hudson, J. D. et al. (1999) *J. Exp. Med.* 190:1375–1382
Hudziak, R. M. et al. (1988) *Proc. Natl. Acad. Sci. USA* 85:5102
Husain, et al. (1994) *Cancer Res.* 54:539
Iglesias, M. et al (1998) *Oncogene* 17:1195–1205
Inazuka, M. et al. (1995a) *Ann. Oncol.* 6(9):871–881
Jackman, A. L. et al. (1995b) *Anticancer Drug Des.* 10:573
Jin, S. et al. (2000) *Oncogene* 17(35):4050–7
Johnson, P. G. et al. (1997) *J. Clin. Oncol.* 15:1923–1931
Jones, R. G and Mann, M. J. (1953) *J. Am. Cancer Soc.* 75: 4048–4052
Kashani-Sabet et al. (1988) *Cancer Res.* 48:5775–5778
Kitasato, H. et al. (2000) *Arthritis Rheum.* 43(2):469–70
Knudson, A. G. (1993) *Proc. Natl. Acad. Sci. USA* 90(23): 10914–21
Kobayashi, H. et al. (1995) *Japan. J. Cancer Res.* 86:1014–1018
Krajewskas and Shugar (1982) *Biochem. Pharmacol.* 31(6): 1097–1102
Kullmann, F. et al. (1999) *Arthritis Rheum.* 42(8):1594–600
Lang, S. M. et al (1999) *Gut.* 44:822–825
Lasic, D. D. (1996) *Nature* 380:561–562
Lee, V. et al. (1997) *Exp. Cell Res.* 234:270–276
Lenz, H. J. etal. (1998) *Clin. Cancer Res.* 4:1227–1234
Les, A. et al. (1988) *Bio. Structure and Dynamics* 15(4): 703–715
Lewis, J. G. et al. (1996) *Proc. Natl. Acad. Sci. USA* 93:3176–3181
Lin, W. Y et al. (1997) *Eur. J. Nucl. Med.* 24:590–595
Livak, K. J. et al. (1992) *Nucleic Acids Res.* 20:4831–4837
Lönn, U. et al. (1996) *Cancer* 77(1):107–112
Look, K. Y. et al. (1997) *Anticancer Res.* 17:2353–2356
Lovejoy, etal. (1997) *J. Pathol.* 181:130–135
Madec, A. et al. (1988) *Bull. Cancer* 75:187–194
Mader, R. M. et al. (1998) *Gen. Pharmacol.* 31(5):661–666
Malfait, A. M. et al. (2000) *PNAS* 97(17):9561–9566
Marinova-Mutafchieva, L. et al.(2000) *Arthritis and Rheumatism* 43(3):638–644
Masciullo, V., et al. (2000) *Int. J. Oncol.* 17(5):897–902
McGuigan, C. (1993) *J. Med. Chem.* 36:1048–1052
McGuigan, C. (1996) *J. Med. Chem.* 39:1748–1753
McGuigan, C. et al. (1994) *FEBS Lett.* 351:11–14
McIntee, E. J. (1997) *J. Med. Chem.* 40:3323–3331
Meier, et al. (1997) *Bioorg. Med. Chem. Lett.* 7:1577
Meier, et al. (1997) *Bioorg. Med. Chem. Lett.* 7:99
Meier, et al. (1997) *International Antiviral News.* 5:183
Melton, R. G. and Sherwood, R. E. (1996) *J. Natl. Cancer Inst.* 88:153–165
Michael, V. V., et al. (2000) *Front. Biosci.* 5D:594–601
Miller, E. J. (1972) *Biochemistry* 11:4903–4909
Miller, J. H. "A short course in bacterial genetics: A laboratory manual and handbook for *E. coli* and related bacteria" Cold Spring Harbor Press (1992)
Miotla, J. et al. (2000) *Laboratory Investigation* 80(8): 1195–1205
Morgan, A. S. et al. (1998) *Cancer Res.* 58:2568–2575
Mountz, J. D. et al. (1994) *Arthritis& Rheumatism* 37(10): 1415–1422
Negishi, et al. (1996) *Nuc. Acids Symp. Ser.* 35:137–138
Paradiso, A. et al. (2000) *Br. J. Cancer* 82(3):560–567
Pederson-Lane, J. (1997) *Protein Expression and Purification* 10:256–262
Pegram, M. D. et al. (1997) *Oncogene* 15:537–547
Phelps, M. E. et al. (1980) *J. Med. Chem.* 23:1229–1232
Plath, T. et al. (2000) *J. Cell. Biol.* 150(6):1467–78
Pluta, et al. (1999) *Boll. Chim. Farm.* 138(1):30–33
Portwine, C. (2000) *Pediatr. Res.* 47(5)573
Reme, T. et al. (1998) *Clin. Exp. Immunol.* 111(2):353–8
Robins, M. J. et al. (1981) *Tetrahedron Lett.* 22:421–424
Robins, M. J. et al. (1982) *Can. J. Chem.* 60:554–557
Robins, M. J. et al. (1983) *J. Org. Chem.* 48:1854–1862
Romain, S. et al. (1995) *Intl. J. Cancer* 61(1):7–12
Roth, J. A. et al. (1999) *Oncology* 13(10 Supp. 5):148–154
Ruth, J. L. et al. (1978) *J. Org. Chem.* 43:2870–2876
Saboulard, L. et al. (1999) *Mol. Pharm.* 56:693–704
Santi, D. V. (1980) *J. Med. Chem.* 23:103–111
Sastry, et al. (1992) *Mol. Pharmacol.* 41:441–445
Schaechter, M. et al., eds. (1993) Mechanisms of Microbial Disease, $2^{nd}$ Ed., Williams and Wilkins
Shepard, H. M. et al. (1988) *J. Clin. Immunol.* 8:353–395
Shim, J. et al. (2000) *J. Biol. Chem.* 275(19):14107–11
Simon, L. S. (2000) *Int. J. Clin. Pract.* 54(4):243–9
Simon, S. M. and Schindler, M. (1994) *Proc. Natl. Acad. Sci. USA* 91:3497
Smith, K. A. et al. (1995) *Philos. Trans. R. Soc. Lon. B. Biol. Sci* 347:49–56
Spector, D. L. et al. (1998) Cells, A Laboratory Manual, Vols I to III, Cold Spring Harbor Press
Stühlinger, M. et al. (1994) *J. Steroid Biochem.* 49:39
Sugarman, B. J. et al. (1985) *Science* 230:943–945
Suki, S. et al. (1995) *Leukemia Lymphoma* 18(1–2):87–92
Sun, Y. et al. (2000) *J. Biol. Chem.* 275(15):11327–32
Sun, Y. et al. (1999) *J. Biol. Chem.* 274(17):11535–40
Suzui, M. et al. (1995) *Molecular Carcinogenesis* 12:193–197
Tak, P. P. et al. (2000) *Immunol. Today* 21(2):78–82
Tanaka, K. et al. (1999) *Circulation* 99(13):1656–1659
Tannock, I. F. (1996) *J. Clin. Oncol.* 14(12):3156–3174
Teh, B. T. (1999) *Anticancer Res.* 19(6A):4715–4728
Tolstikov, V. V. et al. (1997) *Nucleosides Nucleotides* 16:215–225
Troutner, D. A. (1987) *Nucl. Med. Biol.* 14:171–176
Valette, et al. (1996) *J. Med. Chem.* 39:1981
Voet, et al. (1995) *Biochemistry* $2^{nd}$ Ed., John Wiley & Sons, Inc.
Wahba, A. J. et al. (1961) *J. Biol. Chem.* 236(3):C11
Wallis, et al. (1999) *Farmaco* 54(1–2):83–89
Wataya, Y. (1979) *J. Med. Chem.* 22:339–340
Weinberg, R. A. (1995) *Acad. Sci.* 758:331–8
Wettergren, Y. et al. (1994) *Mol. Genet.* 20:267–285
Whalen and Boyer (1998) *Semin. Liver Dis.* 18(4):345–358
Wilson, J. D. et al. (eds.) "Harrison's Principles of Internal Medicine" $12^{th}$ ed., McGraw-Hill, Inc., pp. 21–76 (1991)
Wolff, B. and Naumann, M. (1999) *Oncogene* 18:2663–2666
Yang, A. et al. (2000) *Nature* 404:99–103
Yen, Y. etal. (1994) *Cancer Res.* 54:3686–3691
Zeid, et al. (1999) *Nucleosides Nucleotides* 18(1):95–111
Zhang, L. et al. (2000) *Cancer Research* 60:3655–3661
Zhao, R. et al. (2000) *Gene Dev* 14(8):981–93

What is claimed is:

1. A method for treating a subject having rheumatoid arthritis comprising delivering to the subject an effective amount of an L- or D-compound of the formula:

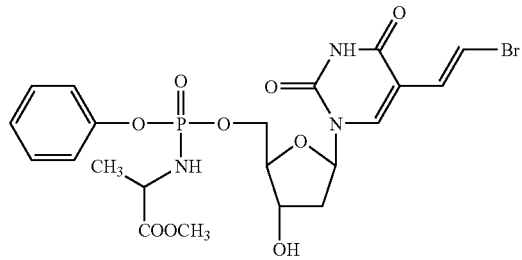

or its 5' monophosphate derivative, and wherein the compound or its 5' monophosphate derivative may be in any of its enantiomeric, disasteriomeric, stereoisomeric or anomeric forms.

2. The method of claim 1, wherein the compound is an L- or D-compound of the formula:

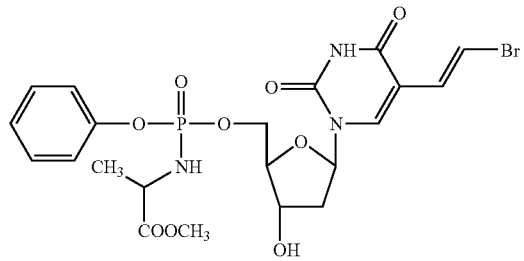

and wherein the compound may be in any of its enantiomeric, disasteriomeric, sterioisomeric or anomeric forms.

* * * * *